(12) United States Patent
She et al.

(10) Patent No.: US 7,847,069 B2
(45) Date of Patent: Dec. 7, 2010

(54) ANTIBODIES AGAINST SUMO4 POLYPEPTIDES

(75) Inventors: Jin-Xiong She, Martinez, GA (US); Cong-Yi Wang, Martinez, GA (US)

(73) Assignee: Medical College of Georgia Research Institute, Augusta, GA (US)

( * ) Notice: Subject to any disclaimer, the term of this patent is extended or adjusted under 35 U.S.C. 154(b) by 361 days.

(21) Appl. No.: 11/671,464

(22) Filed: Feb. 5, 2007

(65) Prior Publication Data

US 2007/0225480 A1 Sep. 27, 2007

Related U.S. Application Data

(62) Division of application No. 11/090,906, filed on Mar. 25, 2005, now Pat. No. 7,173,119.

(60) Provisional application No. 60/556,406, filed on Mar. 25, 2004.

(51) Int. Cl.
*C07K 16/00* (2006.01)
(52) U.S. Cl. .................................. 530/387.9
(58) Field of Classification Search ............. None
See application file for complete search history.

(56) References Cited

U.S. PATENT DOCUMENTS

2002/0048763 A1 4/2002 Penn et al.

FOREIGN PATENT DOCUMENTS

WO WO 01/57278 A2 8/2001

OTHER PUBLICATIONS

Saitoh, H. and Hinchey, J. J. Biol. Chem. 2000;275(9):6252-6258.*
Bohren, K.M., et al. J. Biol. Chem. 2004;279(26):27233-27238.*
Davies, J. L. et al., 1994, "A genome-wide search for human Type 1 diabetes susceptibility genes," Nature 371:130-136.
Delepine, M. et al., 1997, "Evidence of a non-MHC susceptibility locus in type I diabetes linked to HLA on chromosome 6," Am. J. Hum. Genet. 60:174-187.
Eckenrode, S. et al., 2000, "Fine-mapping of the Type 1 diabetes locus (IDDM4) on chromosome 11q and evaluation of two candidate genes (FADD and GALN) by affected sibpair and linkage-disequilibrium analyses," Hum.Genet. 106:14-18.
Edlund et al., 1985, "Cell specific expression of the rat insulin gene: evidence for role of two distinct 5' flanking elements," Science 230:912-916.
Guo et al., 2004, "A functional variant of SUMO4, a new IkBa modifier, is associated with type 1 diabetes," Nature Genetics, 36(8):837-41.
Luo, D. F. et al., 1995, "Affected-sib-pair mapping of a novel susceptibility gene to insulin-dependent diabetes mellitus (IDDM8) on chromosome 6q25-q27," Am. J. Hum. Genet. 57:911-919.
Luo, D. F. et al., 1996, "Confirmation of three susceptibility genes to insulin-dependent diabetes mellitus: IDDM4, IDDM5 and IDDM8," Hum. Mol. Genet. 5:693-698.
Mashreghi-Mohammadi, Gen Embl. No. ALO31133, Mar. 4, 2003.
Nakagawa, Y. et al., 1998, "Fine mapping of the diabetes-susceptibility locus, IDDM4, on chromosome 11q13," Am. J. Hum. Genet. 63:547-556.
Owerbach, D., 2000, "Physical and genetic mapping of IDDM8 on chromosome 6q27," Diabetes 49:508-512.
Poustka et al., GenBank BX508633, Sep. 4, 2003.
Twells, R. C. et al., 2001, "The sequence and gene characterization of a 400-kb candidate region for IDDM4 on chromosome 11q13," Genomics 72:231-242.
Twells, R. C. et al., 2003, "Linkage and association mapping of the LRP5 locus on chromosome 11q13 in Type 1 diabetes," Hum. Genet. 113:99-105.

* cited by examiner

*Primary Examiner*—G. R Ewoldt
(74) *Attorney, Agent, or Firm*—Sutherland Asbill & Brennan LLP

(57) ABSTRACT

Antibodies selectively directed against SUM04 polypeptides are provided. The antibodies are useful research tools and further in the diagnosis and treatment of Type 1 diabetes.

6 Claims, 12 Drawing Sheets

FIGURE 7
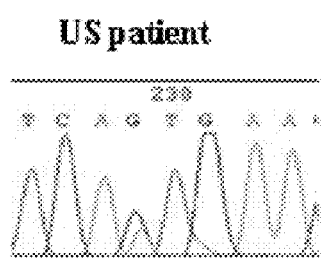
FIGURE 7A
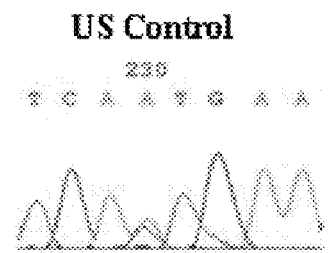
FIGURE 7B
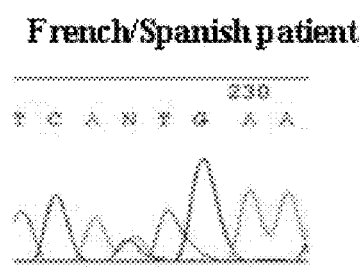
FIGURE 7C
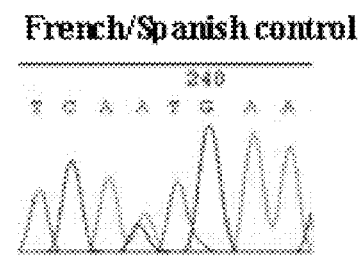
FIGURE 7D
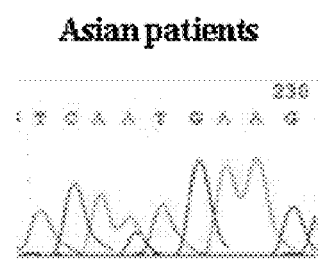
FIGURE 7E
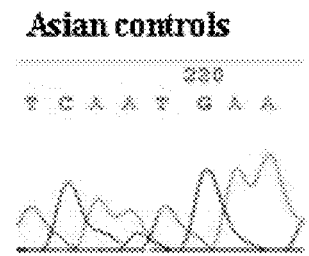
FIGURE 7F

US 7,847,069 B2

SEQUENCE LISTING

<160> NUMBER OF SEQ ID NOS: 26

<210> SEQ ID NO 1
<211> LENGTH: 288
<212> TYPE: DNA
<213> ORGANISM: Homo sapiens

<400> SEQUENCE: 1
atggccaacg aaaagcccac agaagaagtc aagactgaga acaacaatca tattaatttg      60
aaggtggcgg gacaggatgg ttctgtggtg cagtttaaga ttaagaggca gacaccactt     120
agtaaactaa tgaaagccta ttgtgaacca cggggattgt cagtgaagca gatcagattc     180
cgatttggtg ggcaaccaat cagtggaaca gacaaacctg cacagttgga aatggaagat     240
gaagatacaa ttgatgtgtt tcaacagcct acgggaggtg tctactga                  288

<210> SEQ ID NO 2
<211> LENGTH: 95
<212> TYPE: PRT
<213> ORGANISM: Homo sapiens

<400> SEQUENCE: 2

Met Ala Asn Glu Lys Pro Thr Glu Glu Val Lys Thr Glu Asn Asn Asn
 1               5                  10                  15

His Ile Asn Leu Lys Val Ala Gly Gln Asp Gly Ser Val Val Gln Phe
             20                  25                  30

Lys Ile Lys Arg Gln Thr Pro Leu Ser Lys Leu Met Lys Ala Tyr Cys
         35                  40                  45

Glu Pro Arg Gly Leu Ser Val Lys Gln Ile Arg Phe Arg Phe Gly Gly

```
            50                  55                  60
Gln Pro Ile Ser Gly Thr Asp Lys Pro Ala Gln Leu Glu Met Glu Asp
 65                  70                  75                  80

Glu Asp Thr Ile Asp Val Phe Gln Gln Pro Thr Gly Gly Val Tyr
                 85                  90                  95

<210> SEQ ID NO 3
<211> LENGTH: 288
<212> TYPE: DNA
<213> ORGANISM: Homo sapiens

<400> SEQUENCE: 3
atggccaacg aaaagcccac agaagaagtc aagactgaga caacaatca tattaatttg      60 aaggtggcgg gacaggatgg ttctgtggtg cagtttaaga ttaagaggca gacaccactt    120
agtaaactaa tgaaagccta ttgtgaacca cggggattgt caatgaagca gatcagattc    180
cgatttggtg gcaaccaat cagtggaaca gacaaacctg cacagttgga aatggaagat     240
gaagatacaa ttgatgtgtt tcaacagcct acgggaggtg tctactga                 288

<210> SEQ ID NO 4
<211> LENGTH: 95
<212> TYPE: PRT
<213> ORGANISM: Homo sapiens

<400> SEQUENCE: 4

Met Ala Asn Glu Lys Pro Thr Glu Glu Val Lys Thr Glu Asn Asn Asn
 1               5                  10                  15

His Ile Asn Leu Lys Val Ala Gly Gln Asp Gly Ser Val Val Gln Phe
                 20                  25                  30

Lys Ile Lys Arg Gln Thr Pro Leu Ser Lys Leu Met Lys Ala Tyr Cys
             35                  40                  45

Glu Pro Arg Gly Leu Ser Met Lys Gln Ile Arg Phe Arg Phe Gly Gly
         50                  55                  60

Gln Pro Ile Ser Gly Thr Asp Lys Pro Ala Gln Leu Glu Met Glu Asp
 65                  70                  75                  80

Glu Asp Thr Ile Asp Val Phe Gln Gln Pro Thr Gly Gly Val Tyr
                 85                  90                  95

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggattgtca atgaagcaga t                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggattgtca gtgaagcaga t                                               21
```

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtgaaccac ggggattgtc g                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagtagaca cctcccgtag                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggccaacga aaagcccaca                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tccactgatt ggttgcccac                                                20

<210> SEQ ID NO 11
<211> LENGTH: 702
<212> TYPE: DNA
<213> ORGANISM: Homo sapiens

<400> SEQUENCE: 11
gaagcagcag ctgaggagac tccggtgttc accatggcca acgaaaagcc cacagaagaa     60
gtcaagactg agaacaacaa tcatattaat ttgaaggtgg cgggacagga tggttctgtg    120
gtgcagtttt agattaagag gcagacacca cttagtaaac taatgaaagc ctattgtgaa    180
ccacggggat tgtcaatgaa gcagatcaga ttccgatttg gtgggcaacc aatcagtgga    240
acagacaaac ctgcacagtt ggaaatggaa gatgaagata caattgatgt gtttcaacag    300
cctacgggag gtgtctactg aaaagggaac ctgcttcttt actccagaac gctgttcttt    360
aaagaccaag attactgcat tctcaattag aaaactgcaa tttggttcca ccacattctg    420
actactacag tatagttttc tctattcttt tgtttccccc ttccacattc ttttattata    480
catgaagtaa ctggtatgtg tacacaagca tattgctttt ttcttcaaac caaacagcca    540
atggtatgtt tgattgaca tcaagtggag acaggatggg aaaaaatact gattctgtga    600
```

```
aaataccccc tttatccatt agtggcatgt tcattcaggt cttatcttta tattctagta      660
agttattttg ctctcactgt tttaacaaaa aaaaaaaaaa aa                         702

<210> SEQ ID NO 12
<211> LENGTH: 15
<212> TYPE: DNA
<213> ORGANISM: Homo sapiens

<400> SEQUENCE: 12
ttagggaagt tcccc                                                        15

<210> SEQ ID NO 13
<211> LENGTH: 49
<212> TYPE: DNA
<213> ORGANISM: Homo sapiens

<400> SEQUENCE: 13
tgaatggatt ttaaaaacag atctggcagc agccaatggg aggccccaa                   49

<210> SEQ ID NO 14
<211> LENGTH: 97
<212> TYPE: PRT
<213> ORGANISM: Homo sapiens

<400> SEQUENCE: 14
```

Met Ser Asp Gln Glu Ala Lys Pro Ser Thr Glu Asp Leu Gly Asp Lys
 1               5                  10                  15

Lys Glu Gly Glu Tyr Ile Lys Leu Lys Val Ile Gly Gln Asp Ser Ser
             20                  25                  30

Glu Ile His Phe Lys Val Lys Met Thr Thr His Leu Lys Lys Leu Lys
         35                  40                  45

Glu Ser Tyr Cys Gln Arg Gln Gly Val Pro Met Asn Ser Leu Arg Phe
     50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Gly
                 85                  90                  95

Gly

```
<210> SEQ ID NO 15
<211> LENGTH: 92
<212> TYPE: PRT
<213> ORGANISM: Homo sapiens

<400> SEQUENCE: 15
```

Met Ser Glu Glu Lys Pro Lys Glu Gly Val Lys Thr Glu Asn Asp His
 1               5                  10                  15

Ile Asn Leu Lys Val Ala Gly Gln Asp Gly Ser Val Val Gln Phe Lys
             20                  25                  30

Ile Lys Arg His Thr Pro Leu Ser Lys Leu Met Lys Ala Tyr Cys Glu
         35                  40                  45

Arg Gln Gly Leu Ser Met Arg Gln Ile Arg Phe Arg Phe Asp Gly Gln
     50                  55                  60

Pro Ile Asn Glu Thr Asp Thr Pro Ala Gln Leu Glu Met Glu Asp Glu
 65                  70                  75                  80

Asp Thr Ile Asp Val Phe Gln Gln Gln Thr Gly Gly
                 85                  90

-continued

```
<210> SEQ ID NO 16
<211> LENGTH: 93
<212> TYPE: PRT
<213> ORGANISM: Homo sapiens

<400> SEQUENCE: 16

Met Ala Asp Glu Lys Pro Lys Glu Gly Val Lys Thr Glu Asn Asn Asp
 1               5                  10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly
                85                  90

<210> SEQ ID NO 17
<211> LENGTH: 93
<212> TYPE: PRT
<213> ORGANISM: Rattus norvegicus

<400> SEQUENCE: 17

Met Ala Asp Glu Lys Pro Lys Glu Gly Val Lys Thr Glu Asn Asn Asp
 1               5                  10                  15

His Ile His Leu Arg Val Ala Gly Gln Asp Gly Ser Val Val Gln Phe
            20                  25                  30

Glu Ile Lys Arg His Thr Pro Leu Ser Lys Leu Met Lys Ala His Cys
        35                  40                  45

Glu Arg Gln Gly Leu Ser Met Arg Gln Ile Arg Phe Pro Phe Asp Gly
    50                  55                  60

Gln Pro Ile Asn Glu Thr Asp Thr Pro Ala Gln Leu Glu Met Glu Asp
65                  70                  75                  80

Glu Asp Thr Thr Asp Met Phe Gln Gln Gln Thr Gly Gly
                85                  90

<210> SEQ ID NO 18
<211> LENGTH: 92
<212> TYPE: PRT
<213> ORGANISM: Xenopus laevis

<400> SEQUENCE: 18

Met Ser Glu Glu Lys Pro Lys Glu Gly Val Lys Thr Glu Asn Asp His
 1               5                  10                  15

Ile Asn Leu Lys Val Ala Gly Gln Asp Gly Ser Val Val Gln Phe Lys
            20                  25                  30

Ile Lys Arg His Thr Pro Leu Ser Lys Leu Met Lys Ala Tyr Cys Asp
        35                  40                  45

Arg Gln Gly Leu Ser Met Arg Gln Ile Arg Phe Arg Phe Asp Gly Gln
    50                  55                  60

Pro Ile Asn Glu Thr Asp Thr Pro Ala Gln Leu Glu Met Glu Asp Glu
65                  70                  75                  80

Asp Thr Ile Asp Val Phe Gln Gln Gln Thr Gly Gly
                85                  90

<210> SEQ ID NO 19
```

```
<211> LENGTH: 93
<212> TYPE: PRT
<213> ORGANISM: Saccharomyces cerevisiae

<400> SEQUENCE: 19

Met Ala Asp Asp Lys Pro Lys Glu Gly Val Lys Thr Glu Asn Asn Asp
 1               5                  10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly
                85                  90

<210> SEQ ID NO 20
<211> LENGTH: 88
<212> TYPE: PRT
<213> ORGANISM: Drosophila melanogaster

<400> SEQUENCE: 20

Met Ser Asp Glu Lys Lys Gly Gly Glu Thr Glu His Ile Asn Leu Lys
 1               5                  10                  15

Val Leu Gly Gln Asp Asn Ala Val Val Gln Phe Lys Ile Lys Lys His
            20                  25                  30

Thr Pro Leu Arg Lys Leu Met Asn Ala Tyr Cys Asp Arg Ala Gly Leu
        35                  40                  45

Ser Met Gln Val Val Arg Phe Arg Phe Asp Gly Gln Pro Ile Asn Glu
    50                  55                  60

Asn Asp Thr Pro Thr Ser Leu Glu Met Glu Glu Gly Asp Thr Ile Glu
65                  70                  75                  80

Val Tyr Gln Gln Gln Thr Gly Gly
                85

<210> SEQ ID NO 21
<211> LENGTH: 93
<212> TYPE: PRT
<213> ORGANISM: Arabidopsis thaliana

<400> SEQUENCE: 21

Met Ser Ala Asn Gln Glu Glu Asp Lys Lys Pro Gly Asp Gly Gly Ala
 1               5                  10                  15

His Ile Asn Leu Lys Val Lys Gly Gln Asp Gly Asn Glu Val Phe Phe
            20                  25                  30

Arg Ile Lys Arg Ser Thr Gln Leu Lys Lys Leu Met Asn Ala Tyr Cys
        35                  40                  45

Asp Arg Gln Ser Val Asp Met Asn Ser Ile Ala Phe Leu Phe Asp Gly
    50                  55                  60

Arg Arg Leu Arg Ala Glu Gln Thr Pro Asp Glu Leu Asp Met Glu Asp
65                  70                  75                  80

Gly Asp Glu Ile Asp Ala Met Leu His Gln Thr Gly Gly
                85                  90

<210> SEQ ID NO 22
<211> LENGTH: 96
```

```
<212> TYPE: PRT
<213> ORGANISM: Lycopersicon esculentum

<400> SEQUENCE: 22

Met Ser Ala Ser Gly Gly Thr Gly Asp Glu Asp Lys Lys Pro Asn Asp
 1               5                  10                  15

Gln Met Val His Ile Asn Leu Lys Val Lys Gly Gln Asp Gly Asn Glu
             20                  25                  30

Val Phe Phe Arg Ile Lys Arg Ser Thr Gln Met Arg Lys Leu Met Asn
         35                  40                  45

Ala Tyr Cys Asp Arg Gln Ser Val Asp Met Asn Ser Ile Ala Phe Leu
     50                  55                  60

Phe Asp Gly Arg Arg Leu Arg Ala Glu Gln Thr Pro Asp Glu Leu Glu
 65                  70                  75                  80

Met Glu Glu Gly Asp Glu Ile Asp Ala Met Leu His Gln Thr Gly Gly
                 85                  90                  95

<210> SEQ ID NO 23
<211> LENGTH: 96
<212> TYPE: PRT
<213> ORGANISM: Oryza sativa

<400> SEQUENCE: 23

Met Ser Ala Ala Gly Glu Glu Asp Lys Lys Pro Ala Gly Gly Glu Gly
 1               5                  10                  15

Gly Gly Ala His Ile Asn Leu Lys Val Lys Gly Gln Asp Gly Asn Glu
             20                  25                  30

Val Phe Phe Arg Ile Lys Arg Ser Thr Gln Leu Lys Lys Leu Met Asn
         35                  40                  45

Ala Tyr Cys Asp Arg Gln Ser Val Asp Met Asn Ala Ile Ala Phe Leu
     50                  55                  60

Phe Asp Gly Arg Arg Leu Arg Gly Glu Gln Thr Pro Asp Glu Leu Glu
 65                  70                  75                  80

Met Glu Asp Gly Asp Glu Ile Asp Ala Met Leu His Gln Thr Gly Gly
                 85                  90                  95

<210> SEQ ID NO 24
<211> LENGTH: 93
<212> TYPE: PRT
<213> ORGANISM: Mus musculus

<400> SEQUENCE: 24

Met Ala Asp Glu Lys Pro Lys Glu Gly Val Lys Thr Glu Asn Asn Asp
 1               5                  10                  15

His Ile Asn Leu Lys Val Ala Gly Gln Asp Gly Ser Val Val Gln Phe
             20                  25                  30

Lys Ile Lys Arg His Thr Pro Leu Ser Lys Leu Met Lys Ala Tyr Cys
         35                  40                  45

Glu Arg Gln Gly Leu Ser Met Arg Gln Ile Arg Phe Arg Phe Asp Gly
     50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly
                 85                  90

<210> SEQ ID NO 25
<211> LENGTH: 16
<212> TYPE: DNA
```

-continued

```
<213> ORGANISM: Homo sapiens

<400> SEQUENCE: 25
cttagggaag ttcccc                                                    16

<210> SEQ ID NO 26
<211> LENGTH: 16
<212> TYPE: DNA
<213> ORGANISM: Homo sapiens

<400> SEQUENCE: 26
cttaaaaaag ttaaaa                                                    16
```

ANTIBODIES AGAINST SUMO4 POLYPEPTIDES

CROSS REFERENCE TO RELATED APPLICATIONS

The present application claims priority as a division application of U.S. patent application Ser. No. 11/090,906 which was filed Mar. 25, 2005 now U.S. Pat. No. 7,173,119, and claims the priority benefit of U.S. Provisional Patent Application Ser. No. 60/556,406 filed Mar. 25, 2004, the entire contents of which are hereby incorporated by reference.

GOVERNMENT LICENSE RIGHTS

This invention was made with government support under Grant No. HD37800 awarded by the National Institutes of Health. The government has certain rights in this invention.

BACKGROUND OF THE INVENTION

1. Field of the Invention

This invention relates generally to nucleic acid sequences encoding polypeptides that are associated with Type 1 diabetes. In particular, this invention relates to nucleic acid and amino acid sequences encoding a member of the small ubiquitin-like modifier (SUMO) gene family, and methods of their use to facilitate the diagnosis of patients suffering from type 1 diabetes.

2. Background Art

Diabetes is a chronic condition that affects an individual's ability to manufacture and utilize the hormone insulin, which is necessary for the conversion of food into energy. Patients suffering from diabetes have an increased risk of developing side effects such as blindness, heart disease, kidney failure, and neurological disease. Type 1 diabetes (T1D) (also known as insulin-dependent diabetes (IDDM) or juvenile onset diabetes) is the more severe form of the illness and is defined by the development of ketoacidosis in the absence of insulin therapy. In patients suffering from Type 1 diabetes, the pancreas produces little or no insulin, and therefore, insulin must be injected daily. Non-insulin-dependent diabetes mellitus (NIDDM or type 2 diabetes) is characterized by persistent hyperglycemia but rarely leads to ketoacidosis. Type 2 diabetes generally manifests after age 40, and therefore, is also known as adult onset-type diabetes. Type 2 diabetes can result from genetic defects that cause both insulin resistance and insulin deficiency.

It is believed that there are mutations in a number of genes that likely contribute to Type 1 diabetes. For example, the insulin-dependent diabetes mellitus 1 locus (IDDM1) on chromosome 6 may harbor at least one susceptibility gene for Type 1 diabetes. It is unknown what effect a mutation at this locus has on a patient's risk, however, this region of chromosome 6 also has genes for antigens that normally tell the immune system not to attack itself. In Type 1 diabetes, the body's immune system mounts an immunological assault on its own insulin and the pancreatic cells that manufacture it.

To date, about 10 loci in the human genome have been found that seem to confer susceptibility to Type 1 diabetes, including: 1) a gene at the locus IDDM2 on chromosome 11, and 2) the gene for glucokinase (CCK), an enzyme that is key to glucose metabolism which helps modulate insulin secretion, located on chromosome 7. Some loci, e.g. IDDM4, IDDM5, and IDDM8, have recently been identified as being correlated with susceptibility to Type 1 diabetes (Twells et al., 2003, 72:231-42; Twells et al., 2001; Nakagawa et al., 1998; Eckenrode et al., 2000; Luo et al., 1995; Luo et al., 1996; Owerbach, 2000; Davies, 1994; Delepine, 1997). In particular, IDDM5 was shown to be linked to a 5-cM genomic interval on chromosome 6q25 (Luo et al., 1995; Luo et al., 1996).

Although it is known in the art that many loci correlate with susceptibility to Type 1 diabetes, it is not known what the susceptibility genes are within most of these intervals. Therefore, what is needed in the art are unique nucleic acid and polypeptide sequences that are associated with Type 1 diabetes. Also needed are methods of facilitating the diagnosis of Type 1 diabetes through the use of such nucleic acid sequences, polypeptide sequences, and unique polymorphisms within these sequences, particularly prior to the clinical onset of the disease.

SUMMARY OF THE INVENTION

This invention fulfills in part the need to identify new, unique nucleic acids and polypeptides associated with Type 1 diabetes. In particular, the present invention describes a novel SUMO4 polypeptide (SUMO4) and SUMO4 coding nucleic acid. The SUMO4 polypeptide and coding nucleic acid were originally identified as SUMO-L. The nomenclature has been updated here to refer to SUMO-L as SUMO4.

The present invention provides isolated nucleic acids encoding polypeptides that are associated with Type 1 diabetes. The present invention also provides vectors comprising any one of the described nucleic acids. The present invention further provides novel polypeptides associated with Type 1 diabetes and antibodies specific to these SUMO4 polypeptides.

The present invention provides methods for facilitating the diagnosis or pre-diagnosis of Type 1 diabetes in an individual comprising a) obtaining a nucleic acid sample from the individual; and b) determining the nucleotide present at position 163 of the SUMO4 gene, wherein the presence of a guanine at said position is indicative of increased likelihood of Type 1 diabetes in the individual as compared with an individual having an adenine nucleotide at said position. (163A→G, M55V) The present invention also provides methods for facilitating the diagnosis of Type 1 diabetes in an individual comprising a) obtaining a nucleic acid sample from the individual; and b) determining the nucleotide present at position 163 of the SUMO4 gene, wherein the presence of an adenine at said position is indicative of decreased likelihood of Type 1 diabetes in the individual as compared with an individual having a guanine nucleotide at said position.

The present invention further provides isolated oligonucleotide primers for facilitating the diagnosis of a subject having or at risk of having an increased likelihood for developing Type 1 diabetes. The present invention also provides methods for facilitating the diagnosis of a subject having or at risk of having an increased likelihood for developing Type 1 diabetes, comprising contacting a target nucleic acid of a sample from a subject with a reagent that detects a mutation in the SUMO4 gene, wherein the mutation encodes a methionine to valine substitution at position 55 of the SUMO4 polypeptide; and detecting the substitution, wherein the detection of the substitution is indicative of a subject having or at risk of having an increased likelihood for developing Type 1 diabetes.

The present invention also provides methods for treating a subject suffering from Type 1 diabetes. The present invention also provides pharmaceutical compositions useful for the treatment of Type 1 diabetes, comprising any one of the described isolated nucleic acids and a pharmaceutical carrier.

These and other embodiments of the invention will become apparent to one of skill in the art upon review of the description of the invention.

BRIEF DESCRIPTION OF THE DRAWINGS

FIG. 4A is a graph showing expression of β-galactosidase activity in a yeast two-hybrid system, indicating an interaction between SUMO4 and IκBα in this system. The pCADT7 plasmid is an empty vector control. FIGS. 4B and 4C show results of co-immunoprecipitation experiments. FIG. 4B is a Western blot that was analyzed with a mouse anti-IκBα mAb. FIG. 4C is a Western blot showing the same immunoprecipitates as FIG. 4B, but analyzed by with a mouse His tag-specific mAb. Lane 1 is the immunoprecipitates from HEK293 cells transfected with an empty vector, and lane 2 is the immunoprecipitates from HEK293 cells transfected with His tagged SUMO4. Molecular weight markers and the position of IκBα and its SUMO4-conjugated form (IκBα-SUMO4) are indicated.

FIG. 5A: Luciferase assay results for unstimulated cells. FIG. 5B: Luciferase assay results for TNFα-stimulated cells. SUMO4 expression leads to decrease of NFκB-dependent transcriptional activity (luciferase activity) by a factor of 12.9. The M55V substitution of SUMO4 resulted in 5.5 times higher NFκB-dependent transcriptional activity after TNFα stimulation. Similar results were also obtained with IL1-β.

FIG. 6A shows electrophoretic gels for detection of the RT-PCR products. The IL-12p40 transcript was undetectable in unstimulated PBMC (left panel). However, the same PBMC showed high levels of IL-12p40 expression upon IL-1β stimulation (right panel). FIG. 6B is a graph showing the difference in IL-12p40 mRNA expression for individuals with C/C, A/A and A/G genotypes after IL-1β stimulation.

FIG. 7 shows the results of pooled DNA sequencing results for the M55V of SUMO4. Five patients and five controls from US Caucasian, French, and Chinese populations were included for screening of sequence variations in the SUMO4 genes. The results presented here are sequencing results from pooled DNA samples. Each pooled DNA contains equal amount of DNA from randomly selected patients or controls of each population. The results were further confirmed by sequencing PCR products amplified from DNA of each individual.

FIG. 9 shows the results of a SUMO4 conjugation assay for IκBα.

FIG. 10 is an analysis of the SUMO4 promoter region.

FIG. 11 shows results from a chromatin immunoprecipitation (ChIP) assay for the SUMO4 promoter.

FIG. 12 shows Western and 2D gel results for the SUMO4 immunoprecipitates.

DETAILED DESCRIPTION OF THE INVENTION

Figure 1:
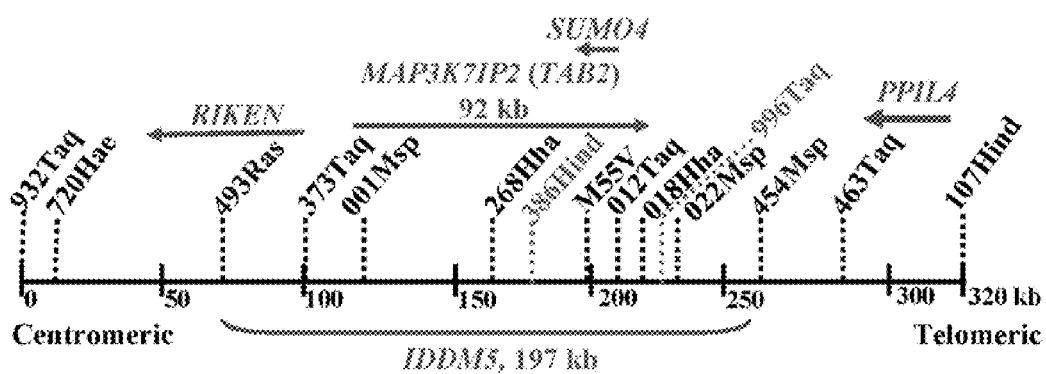
FIG. 1 is a physical and transcription map for the IDDM5 interval. The two single nucleotide polymorphism (SNP) markers that determine the centromeric and telomeric boundaries are shown, along with other SNPs throughout the region. Genes are shown above the map, and the transcriptional direction for each gene is indicated by an arrow.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is further to be understood that unless specifically defined herein, the terminology used herein is to be given its traditional meaning as known in the relative art.

The present invention describes for the first time that the nucleic acid encoding the *Homo sapiens* SUMO4 polypeptide can be used to facilitate the diagnosis of or predisposition to Type 1 diabetes. As used herein, the terms "peptide," "polypeptide," and "protein" refer to a chain of at least four amino acids joined by peptide bonds. The chain may be linear, branched, circular, or combinations thereof. Accordingly, the present invention provides isolated SUMO4 polypeptides. In preferred embodiments, the SUMO4 polypeptide is defined in SEQ ID NO:2 or SEQ ID NO:4.

The SUMO4 polypeptide of the present invention is preferably produced by recombinant DNA techniques. For example, a nucleic acid molecule encoding the polypeptide is cloned into an expression vector, the expression vector is introduced into a host cell, and the SUMO4 polypeptide is expressed in the host cell. The SUMO4 polypeptide can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a SUMO4 polypeptide, or peptide thereof, can be synthesized chemically using standard peptide synthesis techniques. Moreover, native SUMO4 polypeptide can be isolated from cells (e.g., human cells), for example using an anti-SUMO4 polypeptide antibody.

As used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid or polynucleotide molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated SUMO4 nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a human or rat cell). A nucleic acid is also considered isolated if it has been altered by human intervention, or placed in a locus or location that is not its natural site. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1 or SEQ ID NO:3, or a portion thereof, can be isolated using standard molecular biology techniques and the sequence information provided herein. For example, a SUMO4 cDNA can be isolated from a cDNA library using all or portion of one of the sequences of SEQ ID NO:1 or SEQ ID NO:3. Moreover, a nucleic acid molecule encompassing all or a portion of one of the sequences of SEQ ID NO:1 or SEQ ID NO:3 can be isolated by the polymerase chain reaction (PCR)

using oligonucleotide primers designed based upon this sequence. For example, mRNA can be isolated from a cell, and synthetic oligonucleotide primers for PCR amplification can be designed based upon one of the nucleotide sequences shown in SEQ ID NO:1 or SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a SUMO4 nucleotide sequence can be prepared by standard synthetic techniques, e.g., using an automated DNA synthesizer.

The present invention provides an isolated nucleic acid, wherein the nucleic acid comprises a polynucleotide selected from the group consisting of: a) a polynucleotide as defined in SEQ ID NO:1; b) a polynucleotide as defined in SEQ ID NO:3; c) a polynucleotide encoding a polypeptide as defined in SEQ ID NO:2; d) a polynucleotide encoding a polypeptide as defined in SEQ ID NO:4; and e) a polynucleotide complementary to a full-length polynucleotide of any one of a) through d) above. In a preferred embodiment, an isolated nucleic acid molecule of the invention comprises one of the polynucleotide sequences shown in SEQ ID NO:1 or SEQ ID NO:3. In another preferred embodiment, an isolated nucleic acid molecule of the invention comprises a polynucleotide sequence encoding a polypeptide as shown in SEQ ID NO:1 or SEQ ID NO:3. In yet another embodiment, the invention provides an isolated nucleic acid comprises a polynucleotide encoding a polypeptide having at least 88% sequence identity with a polypeptide as defined in SEQ ID NO:2 or SEQ ID NO:4, and wherein the nucleic acid may be used to facilitate the diagnosis of or predisposition to Type 1 diabetes. In yet another embodiment, the invention provides an isolated nucleic acid, wherein the nucleic acid comprises a polynucleotide that hybridizes under highly stringent conditions to a second nucleic acid selected from the group consisting of: a) a nucleic acid comprising a polynucleotide of SEQ ID NO:1 or SEQ ID NO:3; and b) a nucleic acid comprising a polynucleotide that encodes a polypeptide of SEQ ID NO:2 or SEQ ID NO:4, wherein the nucleic acid may be used to facilitate the diagnosis of or predisposition to Type 1 diabetes, and wherein the stringent conditions comprise a hybridization in a 6× sodium chloride/sodium citrate (6×SSC) solution at 65° C. In a preferred embodiment of the present invention, the isolated nucleic acids encode a polypeptide that is capable of interacting with IκBα.

Moreover, the nucleic acid molecule of the invention can comprise a portion of the coding region of one of the sequences in SEQ ID NO:1 or SEQ ID NO:3, for example, a fragment that can be used as a probe or primer or a fragment encoding a biologically active portion of a SUMO4 polypeptide. The nucleotide sequences determined from the cloning of the SUMO4 genes from human cells allow for the generation of probes and primers designed for use in identifying and cloning SUMO4 homologs from other cell types and organisms.

As used herein, the term "biologically active portion of" a SUMO4 polypeptide is intended to include a portion, e.g., a domain/motif, of a SUMO4 polypeptide that participates in the interaction with IκBα. Biologically active portions of a SUMO4 include peptides comprising amino acid sequences derived from the amino acid sequence of a SUMO4 polypeptide, e.g., an amino acid sequence of SEQ ID NO:2 or SEQ ID NO:4, or the amino acid sequence of a polypeptide identical to a SUMO4, which include fewer amino acids than a full length SUMO4 or the full length polypeptide which is identical to a SUMO4 polypeptide, and exhibit at least one activity of a SUMO4 polypeptide. Typically, biologically active portions (e.g., peptides which are, for example, 5, 10, 15, 20, 30, 35, 36, 37, 38, 39, 40, 50, 60, 70, 80, 90, or more amino acids in length) comprise a domain or motif with at least one activity of a SUMO4 polypeptide. As used herein, the term "SUMO4 activity" is intended to include, but is not limited to, the interaction with the IκBα polypeptide and/or the negative regulation of NFκB. As also used herein, the term "IκBα activity" is intended to include, but is not limited to, the negative regulation of NFκB. For the purposes of the present invention, modulation of SUMO4 activity refers to at least a 10% increase or decrease in the SUMO4 activity as compared to the SUMO4 activity in the absence of the SUMO4 polypeptide or peptide.

The invention also provides SUMO4 chimeric or fusion polypeptides. As used herein, a SUMO4 "chimeric polypeptide" or "fusion polypeptide" comprises a SUMO4 operatively linked to a non-SUMO4 polypeptide. A SUMO4 polypeptide refers to a polypeptide having an amino acid sequence corresponding to a SUMO4 polypeptide, whereas a non-SUMO4 polypeptide refers to a polypeptide having an amino acid sequence corresponding to a polypeptide which is not substantially identical to the SUMO4 polypeptide, e.g., a polypeptide that is different from the SUMO4 and is derived from the same or a different organism. With respect to the fusion polypeptide, the term "operatively linked" is intended to indicate that the SUMO4 polypeptide and the non-SUMO4 polypeptide are fused to each other so that both sequences fulfill the proposed function attributed to the sequence used. The non-SUMO4 can be fused to the N-terminus or C-terminus of the SUMO4 polypeptide. For example, in one embodiment, the fusion polypeptide is a GST-SUMO4 fusion polypeptide in which the SUMO4 sequences are fused to the C-terminus of the GST sequences. Such fusion polypeptides can facilitate the purification of recombinant SUMO4 polypeptides. In another embodiment, the fusion polypeptide is a SUMO4 polypeptide containing a heterologous signal sequence at its N-terminus. In certain host cells (e.g. mammalian host cells), expression and/or secretion of a SUMO4 polypeptide can be increased through use of a heterologous signal sequence.

Preferably, a SUMO4 chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). A SUMO4 encoding nucleic acid can be cloned into such an expression vector such that the fusion moiety is linked in-frame to the SUMO4.

In addition to fragments and fusion polypeptides of the SUMO4 polypeptides described herein, the present invention includes homologs and analogs of naturally occurring SUMO4 polypeptides and SUMO4 encoding nucleic acids in the same or other organisms. "Homologs" are defined herein as two nucleic acids or polypeptides that have similar or "identical," nucleotide or amino acid sequences, respectively. Homologs include allelic variants, orthologs, paralogs, agonists, and antagonists of SUMO4 polypeptides as defined hereafter. The term "homolog" further encompasses nucleic acid molecules that differ from one of the nucleotide sequences shown in SEQ ID NO:1 or SEQ ID NO:3 (and portions thereof) due to degeneracy of the genetic code and thus encode the same SUMO4 polypeptide as that encoded by the nucleotide sequences shown in SEQ ID NO:1 or SEQ ID NO:3. As used herein, a "naturally occurring" SUMO4 polypeptide refers to a SUMO4 amino acid sequence that occurs in nature. Preferably, a naturally occurring SUMO4 polypeptide comprises an amino acid sequence as defined in SEQ ID NO:2 or SEQ ID NO:4.

An agonist of the SUMO4 polypeptide can retain substantially the same, or a subset, of the biological activities of the SUMO4 polypeptide. An antagonist of the SUMO4 polypeptide can inhibit one or more of the activities of the naturally occurring form of the SUMO4 polypeptide.

Nucleic acid molecules corresponding to natural allelic variants and analogs, orthologs, and paralogs of a SUMO4 cDNA can be isolated based on their identity to the human SUMO4 nucleic acids described herein using SUMO4 cDNAs, or a portion thereof, as a hybridization probe according to standard hybridization techniques under stringent hybridization conditions. In an alternative embodiment, homologs of the SUMO4 polypeptide can be identified by screening combinatorial libraries of mutants, e.g., truncation mutants, of the SUMO4 for SUMO4 agonist or antagonist activity. In one embodiment, a variegated library of SUMO4 variants is generated by combinatorial mutagenesis at the nucleic acid level and is encoded by a variegated gene library. A variegated library of SUMO4 variants can be produced by, for example, enzymatically ligating a mixture of synthetic oligonucleotides into gene sequences such that a degenerate set of potential SUMO4 sequences is expressible as individual polypeptides, or alternatively, as a set of larger fusion polypeptides (e.g., for phage display) containing the set of SUMO4 sequences therein. There are a variety of methods that can be used to produce libraries of potential SUMO4 homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential SUMO4 sequences. Methods for synthesizing degenerate oligonucleotides are known in the art (See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the SUMO4 coding regions can be used to generate a variegated population of SUMO4 fragments for screening and subsequent selection of homologs of an SUMO4. In one embodiment, a library of coding sequence fragments can be generated by treating a double stranded PCR fragment of a SUMO4 coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the SUMO4 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SUMO4 homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify SUMO4 homologs (Arkin and Yourvan, 1992, PNAS 89:7811-7815; Delgrave et al., 1993, Polypeptide Engineering 6(3):327-331). In another embodiment, cell based assays can be exploited to analyze a variegated SUMO4 library, using methods well known in the art. The present invention further provides a method of identifying a novel SUMO4 polypeptide, comprising (a) raising a specific antibody response to a SUMO4, or a fragment thereof as described herein; (b) screening putative SUMO4 material with the antibody, wherein specific binding of the antibody to the material indicates the presence of a potentially novel SUMO4 polypeptide; and (c) analyzing the bound material in comparison to known SUMO4 polypeptide, to determine its novelty.

As stated above, the present invention includes SUMO4 polypeptides and homologs thereof. To determine the percent sequence identity of two amino acid sequences (e.g., one of the sequences of SEQ ID NO:2 or SEQ ID NO:4, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:2 or SEQ ID NO:4) is occupied by the same amino acid residue as the corresponding position in the other sequence (e.g., a mutant form of the sequence of SEQ ID NO:2 or SEQ ID NO:4), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2 and SEQ ID NO:4. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:2 or SEQ ID NO:4, In other embodiments, the SUMO4 amino acid homologs have sequence identity over at least 15 contiguous amino acid residues, more preferably at least 25 contiguous amino acid residues, and most preferably at least 35 contiguous amino acid residues of SEQ ID NO:2 or SEQ ID NO:4. In another embodiment, the homologs of the present invention are preferably at least about 60-70%, and more preferably at least about 80-85%, 85-90%, or 90-95%, and most preferably at least about 96%, 97%, 98%, 99%, or more identical to SEQ ID NO:2 or SEQ ID NO:4.

In another preferred embodiment, an isolated nucleic acid homolog of the invention comprises a nucleotide sequence which is at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1 or SEQ ID NO:3, or to a portion comprising at least 60 consecutive nucleotides thereof. In one embodiment, the SUMO4 homolog nucleotide sequence is about 80-90% identical to a nucleotide sequence shown in SEQ ID NO:1 or SEQ ID NO:3. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2 or SEQ ID NO:4.

It is further preferred that the isolated nucleic acid homolog of the invention encodes a SUMO4, or portion thereof, that is at least 88% identical to an amino acid sequence of SEQ ID NO:2 or SEQ ID NO:4 and that may function by interacting with the IκBα polypeptide.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1 or SEQ ID NO:3 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1 or SEQ ID NO:3. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:1 or SEQ ID NO:3 and may be used to facilitate the diagnosis of Type 1 diabetes.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. In another embodiment, "highly stringent conditions" refers to hybridization at 65° C. in a 6×SSC solution. Methods for nucleic acid hybridizations are described in Meinkoth and Wahl, 1984, Anal. Biochem. 138: 267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part 1, Chapter 2, Elsevier, N.Y., 1993. Preferably, an isolated nucleic acid molecule of the invention that hybridizes under stringent or highly stringent conditions to a sequence of SEQ ID NO:1 or SEQ ID NO:3 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring human SUMO4.

Using the above-described methods, and others known to those of skill in the art, one of ordinary skill in the art can isolate homologs of the SUMO4 polypeptides comprising amino acid sequences shown in SEQ ID NO:2 or SEQ ID NO:4. One subset of these homologs is allelic variants. As used herein, the term "allelic variant" refers to a nucleotide sequence containing polymorphisms that lead to changes in the amino acid sequences of a SUMO4 and that exist within a natural population. Such natural allelic variations can typically result in 1-5% variance in a SUMO4 nucleic acid. Allelic variants can be identified by sequencing the nucleic acid sequence of interest in a number of different organisms, which can be readily carried out by using hybridization probes to identify the same SUMO4 genetic locus in those organisms. Any and all such nucleic acid variations and resulting amino acid polymorphisms or variations in a SUMO4 polypeptide that are the result of natural allelic variation and that do not alter the functional activity of a SUMO4 polypeptide, are intended to be within the scope of the invention.

Moreover, nucleic acid molecules encoding SUMO4 polypeptides from the same or other species such as SUMO4 analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631-637). Analogs, orthologs, and paralogs of a naturally occurring SUMO4 polypeptide can differ from the naturally occurring SUMO4 polypeptide by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring SUMO4 amino acid sequence, and will exhibit a function similar to a SUMO4 polypeptide. Preferably, a SUMO4 ortholog of the present invention is encoded by a nucleic acid that may be used to facilitate the diagnosis of Type 1 diabetes and/or that may interact with the IκBα polypeptide.

In addition to naturally-occurring variants of a SUMO4 sequence that may exist in the population, the skilled artisan will further appreciate that changes can be introduced by mutation into a nucleotide sequence of SEQ ID NO:1 or SEQ ID NO:3, thereby leading to changes in the amino acid sequence of the encoded SUMO4 polypeptide, without altering the functional activity of the SUMO4 polypeptide. For example, nucleotide substitutions leading to amino acid substitutions at "non-essential" amino acid residues can be made in a sequence of SEQ ID NO:2 or SEQ ID NO:4, A "non-essential" amino acid residue is a residue that can be altered from the wild-type sequence of one of the SUMO4 polypeptides without altering the activity of said SUMO4 polypeptide, whereas an "essential" amino acid residue is required for SUMO4 activity. Other amino acid residues, however, (e.g., those that are not conserved or only semi-conserved in the domain having SUMO4 activity) may not be essential for activity and thus are likely to be amenable to alteration without altering SUMO4 activity.

Accordingly, another aspect of the invention pertains to nucleic acid molecules encoding SUMO4 polypeptides that contain changes in amino acid residues that are not essential for SUMO4 activity. Such SUMO4 polypeptides differ in amino acid sequence from a sequence contained in SEQ ID NO:2 or SEQ ID NO:4, yet retain at least one of the SUMO4 activities described herein. In one embodiment, the isolated nucleic acid molecule comprises a nucleotide sequence encoding a polypeptide, wherein the polypeptide comprises an amino acid sequence at least about 80% identical to an amino acid sequence of SEQ ID NO:2 or SEQ ID NO:4. Preferably, the polypeptide encoded by the nucleic acid molecule is at least about 80-85% identical to one of the sequences of SEQ ID NO:2 or SEQ ID NO:4, more preferably at least about 88-90% or 90-95% identical to one of the sequences of SEQ ID NO:2 or SEQ ID NO:4, and most preferably at least about 96%, 97%, 98%, or 99% identical to one of the sequences of SEQ ID NO:2 or SEQ ID NO:4.

An isolated nucleic acid molecule encoding a SUMO4 having sequence identity with a polypeptide sequence of SEQ ID NO:2 or SEQ ID NO:4 can be created by introducing one or more nucleotide substitutions, additions or deletions into a nucleotide sequence of SEQ ID NO:1 or SEQ ID NO:3, respectively, such that one or more amino acid substitutions, additions, or deletions are introduced into the encoded polypeptide. Mutations can be introduced into one of the sequences of SEQ ID NO:1 or SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a SUMO4 polypeptide is preferably replaced with another amino acid residue from the same side chain family. Alternatively, in another embodiment, mutations can be introduced randomly along all or part of a SUMO4 coding sequence, such as by saturation mutagenesis, and the resultant mutants can be screened for a SUMO4 activity described herein to identify mutants that retain SUMO4 activity. Following mutagenesis of one of the sequences of SEQ ID NO:1 or SEQ ID NO:3, the encoded polypeptide can be expressed recombinantly and the activity of the polypeptide can be determined.

Additionally, optimized SUMO4 nucleic acids can be created. Preferably, an optimized SUMO4 nucleic acid encodes a SUMO4 polypeptide that binds to an IκBα and modulates its activity. As used herein, "optimized" refers to a nucleic acid that is genetically engineered to increase its expression in a given organism. To provide optimized SUMO4 nucleic acids, the DNA sequence of the gene can be modified to 1) comprise codons preferred by highly expressed genes in the organism; 2) comprise an A+T content in nucleotide base composition to that substantially found in the organism; 3) form an initiation sequence for that organism; or 4) to eliminate sequences that cause destabilization, inappropriate polyadenylation, degradation and termination of RNA, or that form secondary structure hairpins or RNA splice sites. Increased expression of SUMO4 nucleic acids in an organism can be achieved by utilizing the distribution frequency of codon usage in a particular organism.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n = 1ZX_n - Y_nX_n$ times $100Z$ where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a SUMO4 nucleic acid can be optimized such that its distribution frequency of codon usage deviates, preferably, no more than 25% from that of highly expressed genes in that organism and, more preferably, no more than about 10%. In addition, consideration is given to the percentage G+C content of the degenerate third base.

In addition to the nucleic acid molecules encoding the SUMO4 polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 88% sequence identity with the polypeptide of SEQ ID NO:2 or SEQ ID NO:4.

The antisense nucleic acid can be complementary to an entire SUMO4 coding strand, or to only a portion thereof. In one embodiment, an antisense nucleic acid molecule is antisense to a "coding region" of the coding strand of a nucleotide sequence encoding a SUMO4. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a SUMO4. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of SUMO4 mRNA, but more preferably is an oligonucleotide that is antisense to only a portion of the coding or noncoding region of SUMO4 mRNA. For example, the antisense oligonucleotide can be complementary to the region surrounding the translation start site of SUMO4 mRNA. An antisense oligonucleotide can be, for example, about 5, 10, 15, 20, 25, 30, 35, 40, 45, or 50 nucleotides in length. Typically, the antisense molecules of the present invention comprise an RNA having 60-100% sequence identity with at least 14 consecutive nucleotides of SEQ ID NO:1 or SEQ ID NO:3, or a polynucleotide encoding a polypeptide of SEQ ID NO:2 or SEQ ID NO:4. Preferably, the sequence identity will be at least 70%, more preferably at least 75%, 80%, 85%, 90%, 95%, or 98%, and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding a SUMO4 to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a SUMO4 polypeptide. As used herein, the term "ribozyme" refers to a catalytic KNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave SUMO4 mRNA transcripts to thereby inhibit translation of SUMO4 mRNA. A ribozyme having specificity for an SUMO4-encoding nucleic acid can be designed based upon the nucleotide sequence of a SUMO4 cDNA, as disclosed herein (i.e., SEQ ID NO:1 or SEQ ID NO:3) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an SUMO4-encoding mRNA. See, e.g., U.S. Pat. Nos. 4,987,071 and 5,116,742 to Cech et al. Alternatively, SUMO4 mRNA can be used to select a catalytic RNA having a specific ribonuclease activity from a pool of RNA molecules. See, e.g., Bartel, D. and Szostak, J. W., 1993, Science 261:1411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2 or SEQ ID NO:4, or a polypeptide having at least 80% sequence identity with a polypeptide of SEQ ID NO:2 or SEQ ID NO:4. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a host cell directly by standard transformation procedures. Alternatively, dsRNA can be expressed in a host cell by transcribing two complementary RNAs.

Other methods for the inhibition of endogenous gene expression, such as triple helix formation (Moser et al., 1987, Science 238:645-650 and Cooney et al., 1988, Science 241:456-459) and co-suppression (Napoli et al., 1990, The Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, Mol. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1 or SEQ ID NO:3. The regions of identity can comprise introns and/or exons and untranslated regions. The introduced sense polynucleotide may be present in the host cell transiently, or may be stably integrated into a host chromosome or extrachromosomal replicon.

Alternatively, SUMO4 gene expression can be inhibited by targeting nucleotide sequences complementary to the regulatory region of a SUMO4 nucleotide sequence (e.g., a SUMO4 promoter and/or enhancer) to form triple helical structures that prevent transcription of a SUMO4 gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In addition to the SUMO4 nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. As used herein, the terms "probe" and "primer" are intended to include oligonucleotides that typically comprise a region of nucleotide sequence that hybridizes under stringent conditions to at least about 12, preferably about 25, more preferably about 40, 50, or 75 consecutive nucleotides of a sense strand of one of the sequences set forth in SEQ ID NO:1 or SEQ ID NO:3; an anti-sense sequence of one of the sequences set forth in SEQ ID NO:1 or SEQ ID NO:3; or naturally occurring mutants thereof. Primers based on a nucleotide sequence of SEQ ID NO:1 or SEQ ID NO:3 can be used in PCR reactions to clone SUMO4 homologs. Probes based on the SUMO4 nucleotide sequences can be used to detect transcripts or genomic sequences encoding the same or substantially identical polypeptides. In preferred embodiments, the probe further comprises a label group attached thereto, e.g. the label group can be a radioisotope, a bioluminescent compound, a chemiluminescent compound, a metal chelate, a fluorescent compound, an enzyme, or an enzyme co-factor. Such probes can be used as a part of a genomic marker test kit for identifying cells which express an SUMO4, such as by measuring a level of an SUMO4-encoding nucleic acid, in a sample of cells, e.g., detecting SUMO4 mRNA levels or determining whether a genomic SUMO4 gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising a SUMO4 nucleic acid as described above, wherein expression of the nucleic acid in a host cell results in modulation of IκBα or NFκB activity as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequencer(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (11990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., SUMO4 polypeptides, mutant forms of SUMO4 polypeptides, fusion polypeptides, etc.).

The recombinant expression vectors of the invention can be designed for expression of SUMO4 polypeptides in prokaryotic or eukaryotic cells. For example, SUMO4 genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423-488; van den Hondel, C. A. M. J. J. et al., 1991, Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991, Annu. Rev. Plant Physiol. Plant Molec. Biol. 42:205-225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes, 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Biolabs, Beverly, Mass.), and pRITS (Pharmacia, Piscataway, N.J.) which fuse glutathione S-transferase (GST), maltose E binding polypeptide, or polypeptide A, respectively, to the target recombinant polypeptide. In one embodiment, the coding sequence of the SUMO4 is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant SUMO4 unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology. Methods in Enzymology 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111-2118). Such alteration of nucleic acid sequences of the invention can be carried out by standard DNA synthesis techniques.

In another embodiment, the SUMO4 expression vector is a yeast expression vector. Examples of vectors for expression in yeast *S. cerevisiace* include pYepSec1 (Baldari, et al., 1987, EMBO J. 6:229-234), pMFa (Kurjan and Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den HondeT, C. A. M. J. J. & Punt, P. J., 1991, "Gene transfer systems and vector development for filamentous fungi," in: Applied Molecular Genetics of Fungi, J. F. Peberdy, et al., eds., p. 1-28, Cambridge University Press: Cambridge.

Alternatively, the SUMO4 polypeptides of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156-2165) and the pVL series (Lucklow and Summers, 1989, Virology 170:31-39).

In yet another embodiment, a SUMO4 nucleic acid of the invention is expressed in mammalian cells using a mammalian expression vector. Examples of mammalian expression vectors include pCDMS (Seed, B., 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733), and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, PNAS 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss, 1990, Science 249:374-379) and the fetopolypeptide promoter (Campes and Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin, and methotrexate. Nucleic acid molecules encoding a selectable marker can be introduced into a host cell on the same vector as that encoding a SUMO4 or can be introduced on a separate vector. Cells stably transfected with the introduced nucleic acid molecule can be identified by, for example, antibiotic selection (e.g., cells that have incorporated the selectable marker gene will survive, while the other cells die).

According to the present invention, the introduced SUMO4 polypeptide may be maintained in the host cell stably if it is incorporated into a non-chromosomal autonomous replicon or integrated into a host cell chromosome. Alternatively, the introduced SUMO4 may be present on an extra-chromosomal non-replicating vector and may be transiently expressed or transiently active.

In one embodiment, a homologous recombinant microorganism can be created wherein the SUMO4 nucleic acid is integrated into a chromosome, a vector is prepared which contains at least a portion of a SUMO4 gene into which a deletion, addition, or substitution has been introduced to thereby alter, e.g., functionally disrupt, the SUMO4 gene. Preferably, the SUMO4 gene is a human SUMO4 gene, but it can be a homolog from a related or unrelated organism. In one embodiment, the vector is designed such that, upon homologous recombination, the endogenous SUMO4 gene is functionally disrupted (i.e., no longer encodes a functional polypeptide; also referred to as a knock-out vector). Alternatively, the vector can be designed such that, upon homologous recombination, the endogenous SUMO4 gene is mutated or otherwise altered but still encodes a functional polypeptide (e.g., the upstream regulatory region can be altered to thereby alter the expression of the endogenous SUMO4). To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene Therapy American Scientist 87(3):240-247).

Whereas in the homologous recombination vector, the altered portion of the SUMO4 gene is flanked at its 5' and 3, ends by an additional nucleic acid molecule of the SUMO4 gene to allow for homologous recombination to occur between the exogenous SUMO4 gene carried by the vector and an endogenous SUMO4 gene. The additional flanking SUMO4 nucleic acid molecule is of sufficient length for successful homologous recombination with the endogenous gene. Typically, several hundreds of base pairs up to kilobases of flanking DNA (both at the 5, and 3' ends) are included in the vector (See e.g., Thomas, K. R., and Capecchi, M. R., 1987, Cell 51:503 for a description of homologous recombination vectors).

In another embodiment, recombinant microorganisms can be produced that contain selected systems that allow for regulated expression of the introduced gene. Such regulatory systems are well known in the art.

Whether present in an extra-chromosomal non-replicating vector or a vector that is integrated into a chromosome, the SUMO4 polynucleotide preferably resides in a mammalian expression cassette. A mammalian expression cassette preferably contains regulatory sequences capable of driving gene expression in mammalian cells that are operatively linked so that each sequence can fulfill its function, for example, termination of transcription by polyadenylation signals.

Gene expression should be operatively linked to an appropriate promoter conferring gene expression in a timely, cell specific, or tissue specific manner. Promoters useful in the expression cassettes of the invention include any promoter that is capable of initiating transcription in a host cell. The promoter may be constitutive, inducible, developmental stage-preferred, cell type-preferred, tissue-preferred, or organ-preferred.

The nucleic acid molecules, polypeptides, polypeptide homologs, fusion polypeptides, primers, vectors, and host cells described herein can be used in one or more of the following methods: evolutionary studies; determination of SUMO4 regions required for function; modulation of SUMO4 activity; and modulation of IκBα or NFκB activity.

In a preferred embodiment, transcription of the SUMO4 nucleic acid is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as a SUMO4 nucleic acid. Therefore, activating and repressing ZFPs can be created that specifically recognize the SUMO4 promoters described above and used to increase or decrease SUMO4 expression. The present invention also includes identification of the homologs of SUMO4 as defined in SEQ ID NO:2 and SEQ ID NO:4, in a target cell, as well as the homolog's promoter. The invention also provides a method of increasing expression of a gene of interest within a host cell as compared to a wild type variety of the host cell, wherein the gene of interest is transcribed in response to SUMO4, comprising: (a) transforming the host cell with an expression vector comprising a SUMO4 coding nucleic acid, and (b) expressing the SUMO4 polypeptide within the host cell, thereby increasing the expression of the gene transcribed in response to the SUMO4 polypeptide, as compared to a wild type variety of the host cell.

The invention further provides a recombinant expression vector comprising a SUMO4 DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a SUMO4 mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a SUMO4 polypeptide can be expressed in bacterial cells such as C. glutamicuni, insect cells, fungal cells, or mammalian cells (such as Chinese hamster ovary cells (CHO) or COS cells), algae, ciliates, plant cells, fungi, or other microorganisms like C. glutamicum. Other suitable host cells are known to those skilled in the art.

A host cell of the invention, such as a prokaryotic or eukaryotic host cell in culture, can be used to produce (i.e., express) a SUMO4 polypeptide. Accordingly, the invention further provides methods for producing SUMO4 polypeptides using the host cells of the invention. In one embodiment, the method comprises culturing the host cell of invention (into which a recombinant expression vector encoding a SUMO4 polypeptide has been introduced, or into which genome has been introduced a gene encoding a wild-type or altered SUMO4 polypeptide) in a suitable medium until the SUMO4 polypeptide is produced. In another embodiment, the method further comprises isolating SUMO4 polypeptides from the medium or the host cell.

The SUMO4 nucleic acid molecules of the invention are also useful for evolutionary and polypeptide structural studies. By comparing the sequences of the nucleic acid molecules of the present invention to those encoding similar polypeptides from other organisms, the evolutionary relatedness of the organisms can be assessed. Similarly, such a comparison permits an assessment of which regions of the sequence are conserved and which are not, which may aid in determining those regions of the polypeptide that are essential for the functioning of the polypeptide. This type of determination is of value for polypeptide engineering studies and may give an indication of what the polypeptide can tolerate in terms of mutagenesis without losing function.

Manipulation of the SUMO4 nucleic acid molecules of the invention may result in the production of SUMO4 polypeptides having functional differences from the wild-type SUMO4 polypeptides. These polypeptides may be improved in efficiency or activity, may be present in greater numbers in the cell than is usual, or may be decreased in efficiency or activity.

Additionally, the sequences disclosed herein, or fragments thereof can be used to generate knockout mutations in the genomes of various organisms. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246-252. The aforementioned mutagenesis strategies for SUMO4 polypeptides are not meant to be limiting; variations on these strategies will be readily apparent to one skilled in the art.

The invention also provides method for facilitating the diagnosis of Type 1 diabetes in an individual comprising a) obtaining a nucleic acid sample from the individual; and b) determining the nucleotide present at position 163 of the SUMO4 gene, wherein the presence of a guanine at said position is indicative of increased likelihood of Type 1 diabetes in the individual as compared with an individual having an adenine nucleotide at said position. In one embodiment, an individual that has an increased likelihood of Type 1 diabetes comprises the SUMO4 gene comprises the nucleotide sequence as defined in SEQ ID NO:1. In certain embodiments, the nucleic acid sample is obtained from a tissue selected from the group consisting of: lymph node, spleen, thymus, liver, tonsil tissue, and isolated cells thereof. In a preferred embodiment, the nucleic acid sample is obtained from a lymph node tissue or cells isolated therefrom.

The invention further provides methods for facilitating the diagnosis of Type 1 diabetes in an individual comprising a) obtaining a nucleic acid sample from the individual; and b) determining the nucleotide present at position 163 of the SUMO4 gene, wherein the presence of an adenine at said position is indicative of decreased likelihood of Type 1 diabetes in the individual as compared with an individual having a guanine nucleotide at said position. In one embodiment, an individual that has an decreased likelihood of Type 1 diabetes comprises the SUMO4 gene comprises the nucleotide sequence as defined in SEQ ID NO:3. In another embodiment, the nucleic acid sample is obtained from a tissue selected from the group consisting of: lymph node, spleen, thymus, liver, tonsil tissue, and isolated cells thereof. In a preferred embodiment, the nucleic acid sample is obtained from a lymph node tissue or cells isolated therefrom.

The present invention also provides isolated oligonucleotide primers for facilitating the diagnosis of a subject having or at risk of having an increased likelihood for developing Type 1 diabetes, wherein the primer detects a mutation encoding a methionine to valine substitution at position 55 of the SUMO4 polypeptide. In a preferred embodiment, the primer specifically hybridizes with a target nucleic acid comprising a polynucleotide sequence selected from the group consisting of: a) TCAA; b) TCAG; and c) the complement of a) or b). In one embodiment, the primer sequence is selected from the group consisting of: a) 5' GGGATTGTCAATGAAGCAGAT 3' (SEQ ID NO:5); b) 5' CGOiGATGTCAGTGAAGCAGAT 3' (SEQ ID NO:6); and c) the complement of a) or b). The present invention provides methods for diagnosis of a subject having or at risk of having an increased likelihood for developing Type 1 diabetes, comprising contacting a target nucleic acid of a sample from a subject with a reagent that detects a mutation in the SUMO4 gene, wherein the mutation encodes a methionine to valine substitution at position 55 of the SUMO4 polypeptide; and detecting the substitution, wherein the detection of the substitution is indicative of a subject having or at risk of having an increased likelihood for developing Type 1 diabetes. In one embodiment, the target nucleic acid is DNA or RNA, and the reagent is a nucleic acid probe. In a preferred embodiment, the target nucleic acid is amplified prior to detection. In a more preferred embodiment, the target nucleic acid is amplified by PCR prior to detection. In another preferred embodiment, the probe comprises a detectable label selected from the group consisting of a radioisotope, a bioluminescent compound, a chemiluminescent compound, a fluorescent compound, a metal chelate, and an enzyme. In another preferred embodiment, the target nucleic acid is present on a microarray.

In another embodiment the present invention provides methods for diagnosis of a subject having or at risk of having an increased likelihood for developing Type 1 diabetes, comprising amplification of the target nucleic acid followed by restriction digestion of the amplified nucleic acid and resolution on a 3% agarose gel. In a preferred embodiment, the primer sequences used to amplify the target nucleic acid are: a) 5'-TGTGAACCACGGGGATTGTCG-3' (SEQ ID NO:7) and b) 5'-TCAGTAGACACCTCCCGTAG-3' (SEQ ID NO:8). In another preferred embodiment, the amplified nucleic acids are digested with a Taq I restriction endonuclease. In one embodiment, the amplified nucleic acid is amplified from a subject that is homozygous for the A allele (i.e. methionine at position 55 of both alleles), or heterozygous for the A allele, and the amplified nucleic acid can be digested. In another embodiment, the amplified nucleic acid is amplified from a subject that is homozygous for the G allele, and the amplified nucleic acid cannot be digested (i.e. vaTine at position 55 of both alleles).

Another aspect of the invention pertains to isolated SUMO4 polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of SUMO4 in which the polypeptide is separated from some of the cellular components of the cells in which it is naturally or recombinantly produced. In one embodiment, the language "substantially free of cellular material" includes preparations of a SUMO4 polypeptide having less than about 30% (by dry weight) of non-SUMO4 polypeptide material (also referred to herein as a "contaminating polypeptide"), more preferably less than about 20% of non-SUMO4 material, still more preferably less than about 10% of non-SUMO4 polypeptide material, and most preferably less than about 5% non-SUMO4 polypeptide material.

When the SUMO4 polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of SUMO4 polypeptide in which the polypeptide is separated from chemical precursors or other chemicals that are involved in the synthesis of the polypeptide. In one embodiment, the language "substantially free of chemical precursors or other chemicals" includes preparations of a SUMO4 having less than about 30% (by dry weight) of chemical precursors or non-SUMO4 chemicals, more preferably less than about 20% chemical precursors or non-SUMO4 chemicals, still more preferably less than about 10% chemical precursors or non-SUMO4 chemicals, and most preferably less than about 5% chemical precursors or non-SUMO4 chemicals. In preferred embodiments, isolated polypeptides, or biologically active portions thereof, lack contaminating polypeptides from the same organism from which the SUMO4 is derived. Typically, such polypeptides are produced by recombinant expression of, for example, a human SUMO4 polypeptide in an organism other than human, or microorganisms such as *C. glutamicum*, ciliates, algae, or fungi.

The present invention also provides antibodies that specifically bind to a SUMO4 polypeptide, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10:169-175). In a preferred embodiment, the antibody that specifically binds a polypeptide as defined in SEQ ID NO:2 will not bind a polypeptide as defined in SEQ ID NO:4. In another preferred embodiment, the antibody that specifically binds a polypeptide as defined in SEQ ID NO:4 will not bind a polypeptide as defined in SEQ ID NO:2.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts, A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

The present invention provides methods of modulating the activity of an IκBα or NFκB polypeptide comprising administering an effective amount of a SUMO4 composition to the IκBα polypeptide or NFκB polypeptide. In one embodiment, the composition comprises a polypeptide encoded by a polynucleotide selected from the group consisting of a polynucleotide as defined in SEQ ID NO:1 or SEQ ID NO:3, a polynucleotide encoding a polypeptide as defined in SEQ ID NO:2 or SEQ ID NO:4, and a polynucleotide complementary to a full-length polynucleotide thereof. In another embodiment, the composition comprises a nucleic acid selected from the group consisting of a polynucleotide as defined in SEQ ID NO:1 or SEQ ID NO:3, a polynucleotide encoding a polypeptide as defined in SEQ ID NO:2 or SEQ ID NO:4, and a polynucleotide complementary to a full-length polynucleotide thereof. In yet another embodiment, the composition comprises an antibody that specifically binds a polypeptide as defined in SEQ ID NO:2 or SEQ ID NO:4.

The compositions of this invention further comprise a pharmaceutically acceptable carrier. The phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein with respect to these methods, the term "administering" refers to various means of introducing a composition into a cell or into a patient. These means are well known in the art and may include, for example, injection; tablets, pills, capsules, or other solids for oral administration; nasal solutions or sprays; aerosols, inhalants; topical formulations; liposomal forms; and the like. As used herein, the term "effective amount" refers to an amount that will result in the desired result and may readily be determined by one of ordinary skill in the art.

The SUMO4 polypeptides, nucleic acids, and antibodies of the present invention may be formulated for parenteral administration, e.g., formulated for injection via the intravenous, intramuscular, sub-cutaneous, transdermal, or other such routes. The preparation of an aqueous composition that contains such a protein or antibody as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The SUMO4 compositions of the present invention can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the polypeptide or nucleic acid admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

In one embodiment, the present invention provides methods for treating a subject having Type 1 diabetes by administering a composition comprising a SUMO4 nucleic acid, polypeptide, or antibody.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Identification of Polymorphism in IDDM5 Associated with Type 1 Diabetes

To narrow down the genomic region of IDDM5 associated with Type 1 diabetes, fine-mapping was performed using a high density of single nucleotide polymorphisms (SNPs) flanking the IDDM5 interval (average of 100 kb per SNP). The initial mapping was carried out with a case-control data set consisting of 703 patients and 916 ethnically and geographically matched controls. There were 244 US Caucasian patients and 274 controls, 170 Spanish patients and 151 controls, 96 Mainland Chinese patients and 188 controls, 96 Taiwanese patients and 191 controls, 97 Korean patients and 112 controls. The study involved a total of 944 multi-ethnic diabetic families: US Caucasian (416 multiplex and 50 simplex families), Italian (46 multiplex and 50 simplex families), French (32 multiplex and 12 simplex families), Spanish (9 multiplex and 9 simplex families), Mexican American (11 multiplex and 88 simplex families), Mainland Chinese (1 multiplex and 50 simplex families), Taiwanese (27 simplex families), Korean (51 simplex families), and British (92 multiplex families). The Medical College of Georgia Human Assurance Committee approved experiments involving human subjects, and informed consent was obtained from all subjects.

A SNP, 001Msp, was found to be associated with Type 1 diabetes. The C allele had a higher frequency in US patients (57.4%) than matched controls (45.6%) (P=0.0006). Consistently, this allele also had a higher frequency in Type 1 diabetes patients from Spain, Korea, Taiwan, and mainland China (See Table 1).

TABLE 1

| Population | N | Genotype | | | Allele | | Penotype | |
| --- | --- | --- | --- | --- | --- | --- | --- | --- |
| | | CC (%) | CT (%) | TT (%) | C | T | C | $P_{Value}$ |
| US Caucasian-P | 244 | 109 (44.6) | 88 (36.0) | 47 (19.4) | 0.627 | 0.373 | 197 (80.3) | 0.00064 |
| US Caucasian-C | 274 | 78 (28.1) | 113 (41.2) | 83 (30.7) | 0.490 | 0.510 | 190 (69.3) | |
| Spanish-P | 170 | 58 (33.3) | 90 (51.7) | 24 (15.0) | 0.606 | 0.394 | 148 (87.1) | NS |
| Spanish-C | 151 | 42 (27.8) | 77 (51.0) | 32 (21.2) | 0.533 | 0.467 | 119 (78.8) | |
| Taiwanese-P | 96 | 13 (13.5) | 56 (58.3) | 27 (28.2) | 0.427 | 0.573 | 69 (71.9) | NS |

TABLE 1-continued

|  |  | Genotype | | | Allele | | Penotype | |
| --- | --- | --- | --- | --- | --- | --- | --- | --- |
| Population | N | CC (%) | CT (%) | TT (%) | C | T | C | $P_{Value}$ |
| Taiwanese-C | 191 | 22 (11.5) | 99 (51.8) | 70 (36.7) | 0.374 | 0.626 | 121 (63.4) | |
| M. Chinese-P | 96 | 33 (34.3) | 44 (45.8) | 19 (19.9) | 0.573 | 0.427 | 77 (80.2) | NS |
| M. Chinese-C | 188 | 35 (18.6) | 86 (44.7) | 69 (36.7) | 0.415 | 0.585 | 121 (64.4) | |
| Korean-P | 97 | 17 (17.5) | 46 (47.4) | 34 (35.1) | 0.412 | 0.588 | 63 (64.9) | NS |
| Korean-C | 112 | 16 (14.3) | 50 (44.6) | 46 (41.1) | 0.366 | 0.634 | 66 (58.9) | |

NS: Not Significant. P: Patients; C: Controls

All statistical analysis was performed using WebSTATISTICA (http://www.statsoftinc.com/webserver.html). All SNPs were tested for Mendelian errors to identify improbable recombination events and genotyping mistakes. Alleles of all SNPs were in Hardy-Weinberg equilibrium (HWE) in non-affected siblings in all families. The TDT was used to assess association. The $\chi^2$ test was used to evaluate the deviation from 50% of the expectation of transmission from heterozygous parents to affected siblings. Extended TDT was used for haplotype association analysis.

The 001Msp SNP was then analyzed in 944 multi-ethnic diabetic families. Transmission/disequilibrium test (TDT) indicated that the C allele was preferentially transmitted to affected children in the US Caucasian ($P=9.7\times10^{-5}$) and French/Spanish populations ($P=0.03$). Mexican American, Italian, and Chinese/Korean patients also showed over-transmissions, although they did not reach statistical significance due to smaller sample sizes. In contrast, allele C showed lower transmission in the UK families (genetic heterogeneity, $P=0.004$), an observation consistent with our previous linkage studies. In the total data set of 944 families, 001Msp showed strong association with T1D ($P=1.6\times10^{-5}$), while the association become much stronger ($P=2.8\times10^{-7}$) when the UK families were excluded from the analysis (See Table 2 and Table 3). Furthermore, preferential transmission was not observed for the C allele in unaffected children, excluding the possibility of segregation distortion.

TABLE 2

Family-based association results for 001Msp

| Familial sets | Transmitted (%) (C allele) | Not-transmitted (%) (G allele) | $\chi^{2, TDT}$ | $P_{TDT}$ |
| --- | --- | --- | --- | --- |
| US Caucasian | 309 (58.5) | 219 (41.5) | 15.34 | $9.7\times10^{-5}$ |
| Mexican American | 66 (57.9) | 48 (42.1) | 2.84 | NS |
| French/Spanish | 50 (61.7) | 31 (38.3) | 4.46 | 0.03 |
| Italian | 72 (55.4) | 58 (44.6) | 1.51 | NS |
| Chinese/Korean | 54 (59.3) | 37 (40.7) | 3.17 | NS |
| UK* | 78 (46) | 92 (54) | 1.15 | NS |
| Total (exclude UK) | 551 (58.4) | 393 (41.6) | 26.4 | $2.8\times10^{-7}$ |
| Total (include UK) | 629 (56.5) | 485 (43.5) | 18.6 | $1.6\times10^{-5}$ |

NS: Not Significant. The UK families showed heterogeneity, P = 0.0036.

Example 2

Association of SNPs in the IDDM5 Genomic Region with Type 1 Diabetes

Thirteen additional SNPs flanking 001Msp and encompassing a 320 kb genomic region were analyzed in all diabetic families to better define the IDDM5 interval. Three SNPs in the middle of the interval (001Msp, 268Hha, and 012Taq) showed very strong association with T1D, but the association declined rapidly from the center to both flanking sides (See Table 3, Table 4, and Table 5). All of the associated SNPs have shown that alleles overtransmitted in families were also enriched in cases versus controls. The association was not due to Hardy-Weinberg disequilibrium. Haplotype analysis was performed using the three SNPs that showed very strong association with T1D (001Msp, 268Hha, and 012Taq). Three haplotypes were identified and extended TDT (ETDT) showed very strong association with T1D ($P=2.3\times10^{-5}$). The centromeric boundary of IDDM5 was defined by 493Ras that was not associated with T1D, while the telomeric boundary was defined by 454Msp with very weak association ($P=0.05$). Therefore, IDDM5 is most likely contained in this 180 kb of genomic region (FIG. 1).

TABLE 3

Association results for SNPs flanking the IDDM5 region

| SNPs | Physical distance (kb) | Associated allele | Transmission of affected offspring (%) | $\chi^{2, TDT}$ | $P_{TDT}$ |
| --- | --- | --- | --- | --- | --- |
| 932Taq | 0 | T | 50.5 | 0.06 | NS |
| 720Hae | 15 | G | 51.0 | 2.58 | NS |
| 493Ras | 70 | C | 50.6 | 1.010 | NS |
| 373Taq | 100 | A | 56.3 | 12.17 | 0.0005 |
| 001Msp | 121 | G | 58.4 | 26.40 | $2.8\times10^{-7}$ |
| 268Hha | 161 | C | 57.3 | 19.50 | $1.0\times10^{-5}$ |
| 012Taq | 205 | G | 57.8 | 19.32 | $1.1\times10^{-5}$ |
| 018Hha | 220 | A | 55.0 | 11.50 | 0.0006 |
| 022Msp | 230 | A | 54.8 | 12.00 | 0.0005 |
| 454Msp | 267 | A | 53.0 | 3.67 | 0.05 |
| 463Taq | 276 | A | 50.1 | 0.05 | NS |
| 107Hind | 320 | A | 50.2 | 0.01 | NS |

As used herein, "NS" denotes "Not Significant." The 944 multi-ethnic T1D families were included in the study. Each SNP showed heterozygosity of more than 20%. All SNPS showed similar frequencies and no HWE distortion in unaffected individuals. The associated alleles were consistent with results from case-control studies because the alleles overtransmitted in families were also enriched in cases versus controls. TDT (transmission/disequilibrium test) was used for association analyses. The PTDT probability values are provided with percentage transmission from heterozygous parents to affected offspring. The ID for SNPs shown in Table 3 are available in the SNP database under accession numbers 652720, 2166493, 563373, 577001, 506268, 237025, 237012, 237018, 377454 and 369643.

TABLE 4

Family-based association results for 268Hha.

| Familial sets | Transmitted (%) (C allele) | Not-transmitted (%) (T allele) | $\chi^{2, TDT}$ | $P_{TDT}$ |
|---|---|---|---|---|
| US Caucasian | 364 (58.4) | 259 (41.6) | 17.70 | $2.3 \times 10^{-5}$ |
| Mexican American | 44 (51.2) | 42 (48.8) | 0.05 | NS |
| French/Spanish | 63 (57.3) | 47 (42.7) | 2.33 | NS |
| Italian | 75 (56.0) | 59 (44.0) | 1.91 | NS |
| Chinese/Korean | 45 (57.0) | 34 (43.0) | 1.53 | NS |
| UK* | 88 (47.8) | 96 (52.2) | 0.35 | NS |
| Total (exclude UK) | 528 (57.3) | 394 (42.7) | 19.50 | $1.0 \times 10^{-5}$ |
| Total (include UK) | 616 (55.7) | 490 (44.3) | 14.35 | $0 \times 10^{-5}$ |

*The UK families showed lower transmissions than random expectation.

TABLE 5

Family-based association results for 012Taq.

| Familial sets | Transmitted (%) (G allele) | Not-transmitted (%) (A allele) | $\chi^{2, TDT}$ | $P_{TDT}$ |
|---|---|---|---|---|
| US Caucasian | 338 (58.7) | 238 (41.3) | 17.36 | $3.09 \times 10^{-5}$ |
| Mexican American | 38 (52.8) | 34 (47.2) | 0.22 | NS |
| French/Spanish | 38 (54.1) | 33 (45.9) | 0.41 | NS |
| Italian | 45 (54.2) | 38 (43.8) | 0.59 | NS |
| Chinese/Korean | 39 (60.0) | 26 (40.0) | 2.6 | NS |
| UK* | 70 (46.1) | 82 (53.9) | 0.95 | NS |
| Total (exclude UK) | 498 (57.4) | 369 (42.6) | 19.19 | $1.1 \times 10^{-5}$ |
| Total (include UK) | 568 (55.7) | 451 (44.3) | 13.43 | 0.00015 |

*The UK families showed lower transmissions than random expectation.

The TAB2 gene appears to be the only known gene within the newly defined IDDM5 region, which spans 92-kb of genomic DNA. TAB2 has been shown to play a pivotal role in the IL-1 signaling pathway (Jiang et al., 2002; Qian et al., 2001; Takaesu et al., 2000; Takaesu et al., 2001). The untranslated and coding regions as well as exon/intron junctions of the TAB2 gene were sequenced using PCR products as template. SNP genotyping was performed by PCR and restriction digestion using methods described previously (Deng et al., 1995). Three SNPs, 001Msp, 268Hhat and 012Taq were found to be located within TAB2 intron sequences and were strongly associated with T1D (Table 3 and FIG. 1), suggesting that TAB2 may be a good candidate gene for IDDM5. Part of a RIKEN sequence, a predicted gene similar to a mouse RIKEN cDNA is located in the interval as well. This gene spans 40-kb of genomic DNA. The 373Taq SNP located in the 5' UTR of the RIKEN sequence is significantly associated with T1D, while the 493Ras SNP located at the center of the gene was not (Table 3 and FIG. 1). Since the promoter region of the RIKEN gene may extend to the region that shows the strongest association, it cannot completely be excluded as a candidate for IDDM5. Furthermore, database searches identified, within intron 6 of the TAB2 gene, another potential transcript with homologies to the small ubiquitin-like modifier (SUMO) gene family (FIG. 1). A series of experiments confirmed that this open reading frame is indeed a novel gene.

Example 3

Characterization of the SUMO4 Gene

A reading frame with homologies to EST markers for the SUMO gene family was identified. To confirm whether it is a real gene, two primers specifically for the reading frame (at least 2 nucleotides are different from the SUMO genes at the 3' ends) were designed to amplify the sequence from cDNA that originated from human spleen polyA RNA (Clontech). PCR amplification yielded a strong expected band from the cDNA, while reactions lacking the reverse transcriptase enzyme generated no product.

The PCR products were then sequenced to confirm that this reading frame is part of a novel gene. 5' and 3' RACE were carried out using a SMART RACE kit (Clontech) according to the manufacturer's instruction, with some modifications as previously reported (Wang et al., 2003). Briefly, for 5'-RACE, the first-strand cDNA synthesis was primed using a gene specific primer, with a SMART oligo also present in the reaction. After the RT reaction an internal gene-specific reverse primer and an UP primer, which is complimentary to the SMART oligo, were used to amplify the 5' end sequence. For 3'-RACE, the first-strand cDNA was synthesized using a modified oligo-dT with an UP oligonucleotide tail. The UP primer and a gene specific forward primer were used for amplification of 3' end sequence. PCR products obtained were directly loaded on to a 2.5% agarose gel, and individual bands were excised from the gel and sequenced with an ABI377 sequencer. This gene showed significant homologies to members of the SUMO gene family, showing 90% nucleotide identity and 87% amino acid identity to SUMO2 (FIG. 2), and very high amino acid and functional property homologies to SUMO1 (data not shown). This novel gene was named SUMO4 (SUMO4).

Example 4

Association of Different SUMO4 and TAB2 Alleles with Type 1 Diabetes

Figure 2:
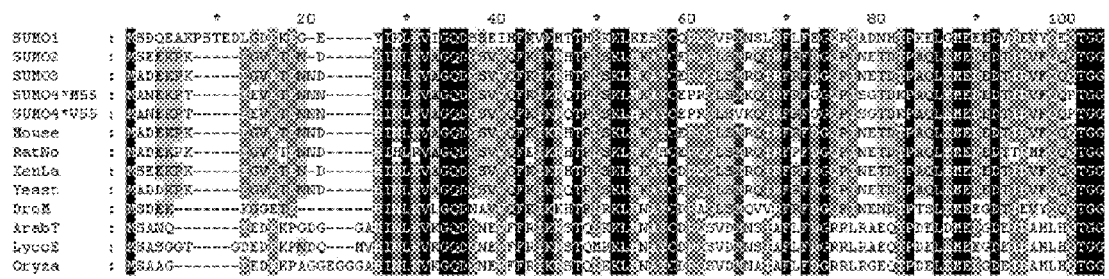
FIG. 2 is a partial amino acid sequence alignment showing homologies between SUMO4 and the SUMO gene family and showing the conservation of Met55 in diverse species. The CUE domain is indicated by a bracket. SUMO4*M55 (residues 1-93 of SEQ ID NO:4) and SUMO4*V55 (residues 1-93 of SEQ ID NO:2) represent SUMO4 with the A and G alleles, respectively. SUMO1 (SEQ ID NO:14), SUMO2 (SEQ ID NO:15), and SUMO3 (SEQ ID NO:16) are other members of the SUMO gene family. Mouse (SEQ ID NO:24) represents a mouse SUMO protein. RatNo (SEQ ID NO:17) represents a SUMO protein from *Rattus norvegicus* and is accession number XP_133787. XenLa (SEQ ID NO:18) is a SUMO protein from *Xenopus laevis* and is accession number AAH154172. The yeast SUMO protein (SEQ ID NO:19) is accession number AAH45271. DroM (SEQ ID NO:20) represents a SUMO protein from *Drosophila melanogaster* (AAD19219). ArabT (SEQ ID NO:21), LycoE (SEQ ID NO:22), and Oryza (SEQ ID NO:23) represent SUMO proteins from *Arabidopsis thaliana* (CAA67923), *Olyza sativa* (BAB86095) and *Lycopersicon esculenturm* (CAB60728), respectively.

Sequence variations in the TAB2 and SUMO4 genes were searched by sequencing 5 patients and 5 controls from US Caucasian, French and Chinese populations, respectively. An A/G SNP was identified within the CUE domain of SUMO4 that results in a methionine to valine (M55V) substitution at position 55 of SUMO4 (M55V) (FIG. 7). Sequence analysis revealed that the methionine at position 55 of SUMO4 is evolutionarily conserved ranging from *Arabidopsis thaliana*, yeast, *Drosophila melanogaster, Xenopus laevis*, mouse to human (FIG. 2). The substitution also changes a PKC phosphorylation site at position 54-56. This M55V SNP is strongly associated with T1D in US case/control cohort with higher frequency of the G (Val) allele in patients (P=0.001). The G allele is also preferentially transmitted from parents to affected children in the US Caucasian (P=0.0017), French/Spanish (P=0.0006), Mexican American (P=0.05) and Chinese/Korean (P=0.04) populations as well as the combined family set (P=1.9×10$^{-7}$) (Table 3, Table 6, and Table 7).

The presence or absence of the SNP in a subject could be detected by amplifying the fragment of the SUMO4 nucleic acid containing the mutation site. PCR was carried out using the following primer sequences: 5' TGTGAACCACGGG-GATTGTCG 3' (SEQ ID NO: 7) and 5' TCAGTAGACAC- CTCCCGTAG 3' (SEQ ID NO: 8) at 94° C. for 2 minutes, then 35 cycles of (94° C. for 30 seconds, 56° C. for 30 seconds, and 72° C. for 30 seconds), then 72° C. for 2 minutes. After PCR amplification, the products were subjected to Taq I digestion according to manufacturer's instructions and resolved on a 3% agarose gel. If the amplified nucleic acid was amplified from a subject that is homozygous for the A allele (i.e. methionine at position 55 of both alleles), the amplified nucleic acid cannot be digested. If the amplified nucleic acid is amplified from a subject that is heterozygous or homozygous for the G allele (i.e. valine at position 55 of one or both alleles), the amplified nucleic acid can be digested.

TABLE 6

Case-Control association results for M55V

| Population | N | Genotype | | | Allele | | Penotype | |
|---|---|---|---|---|---|---|---|---|
| | | GG | GA | AA | G | A | G | $P_{Value}$ |
| US Caucasian-P | 244 | 83 (34.0) | 114 (46.7) | 47 (19.3) | 0.574 | 0.426 | 197 (81.4) | 0.001 |
| US Caucasian-C | 274 | 58 (21.2) | 134 (48.9) | 82 (29.9) | 0.456 | 0.544 | 192 (70.0) | |
| Spanish-P | 170 | 47 (27.6) | 93 (54.7) | 30 (17.7) | 0.550 | 0.450 | 140 (82.3) | N |
| Spanish-C | 151 | 39 (25.8) | 81 (53.6) | 31 (20.6) | 0.526 | 0.474 | 120 (79.5) | |
| Taiwanes -P | 96 | 5 (5.2) | 51 (53.2) | 40 (41.6) | 0.318 | 0.682 | 61 (63.5) | N |
| Taiwanes -C | 191 | 18 (9.4) | 78 (40.8) | 95 (49.8) | 0.298 | 0.702 | 96 (50.2) | |
| M. Chinese-P | 96 | 18 (18.8) | 45 (46.9) | 40 (34.3) | 0.422 | 0.578 | 63 (65.6) | N |
| M. Chinese-C | 188 | 15 (7.9) | 86 (45.7) | 87 (46.4) | 0.308 | 0.692 | 101 (53.7) | |
| Korea -P | 97 | 19 (19.6) | 47 (48.5) | 31 (31.9) | 0.438 | 0.562 | 66 (68.0) | N |
| Korea -C | 112 | 12 (10.7) | 48 (42.9) | 52 (46.4) | 0.321 | 0.679 | 60 (53.6) | |

NS: Not Significant. P: Patients; C:

TABLE 7

Family-based association results for M55V.

| Familial sets | Transmitted (%) (G allele) | Not-transmitted (%) (A allele) | $\chi^{2, TDT}$ | $P_{TDT}$ |
|---|---|---|---|---|
| US Caucasian | 331 (56.5) | 255 (43.5) | 9.87 | 0.0017 |
| Mexican American | 63 (59.4) | 43 (40.6) | 3.77 | 0.05 |
| French/Spanish | 70 (66.7) | 35 (33.3) | 11.67 | 0.0006 |
| Italian | 37 (58.7) | 26 (41.3) | 1.92 | NS |
| Chinese/Korean | 39 (63.0) | 23 (37.0) | 4.13 | 0.04 |
| UK* | 64 (44.0) | 85 (56.0) | 2.95 | NS |
| Total (exclude UK) | 540 (58.6) | 382 (41.4) | 27.08 | $1.95 \times 10^{-7}$ |
| Total (include UK) | 604 (56.4) | 467 (43.6) | 17.52 | $2.87 \times 10^{-5}$ |

*The UK families showed heterogeneity, P = 0.0003.

Two SNPs within the TAB2 gene were also identified. One is a silent mutation in exon 7 (position 2248, G/A, start codon as position 1), and the other is in the 3'-untranslated region (2878, C/G). The 2878C/G SNP is also associated with T1D (P=1.5×10$^{-4}$); however, we were unable to detect an expression difference associated with this SNP, suggesting that this polymorphism is unlikely associated with differential expression. These results prompted us to focus our subsequent studies on the SUMO4 gene and the M55V substitution.

Example 5

Characterization of the M55V Allele of SUMO4

Figure 3:
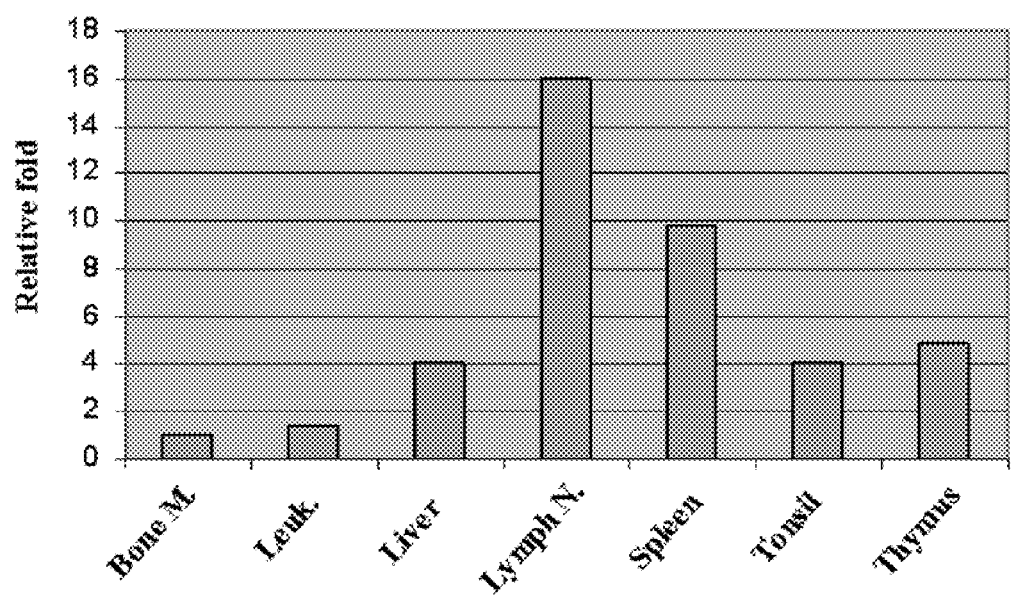
FIG. 3 is a graph showing the relative expression results for SUMO4 in immune related tissues (bone marrow, leukocytes, liver, lymph node, spleen, tonsil, and thymus) by real time PCR.

Due to high DNA homologies between SUMO genes, we used the human immune-related Multiple Tissue cDNA Panel (Clontech) for SUMO4 expression analysis by real time PCR using the Icycler (BioRad). β-actin was used for normalization. The primers used for SUMO4 specific amplification were 5' TGG CCA ACO AAA AGC CCA CA 3' (SEQ ID NO:9) and 5' TCC ACT GAT TGG TnG CCC AC 3' (SEQ ID NO:10). The real-time PCR analysis of the multiple tissue cDNA panel suggested that SUMO4 is highly expressed in immune tissues, with the highest expression in the lymph node and spleen, and the lowest expression in bone marrow (FIG. 3). Previous studies have shown that SUMO is a family of proteins involved in protein post-translational modifications (Best et al., 2002; Joseph et al., 2002; Melehior & Hengst, 2002; Rogers et al., 2002; Ross et al., 2002; Tian et al., 2002; Desterro et al., 1998; Matunis, 2002).

Based on the potential function of SUMO4 as a post-translational modifier, we searched for its modification targets by screening a pretransformed human spleen cDNA library in a yeast two-hybrid system. The Matchmaker Galt4 two-hybrid system 3 kit (Clontech) was used for two-hybrid analyses. The SUMO4 coding sequence was PCR engineered and cloned into the pGBKT7 vector, which was used as a bait to screen a pretransformed human spleen Matchmaker cDNA library at high stringency culture conditions. To confirm the interaction between SUMO4 and IκBα, the full-length IκBα cDNA was cloned into the pGADT7 vector (as targets), which was then co-transformed into an AH109 yeast strain along with the pGBKT7-SUMO4 plasmid. An empty pGADT7 vector was used as a control. The cultures were assayed for β-galactosidase to verify two-hybrid interaction according to the manufacturer's instructions.

Figure 4A:
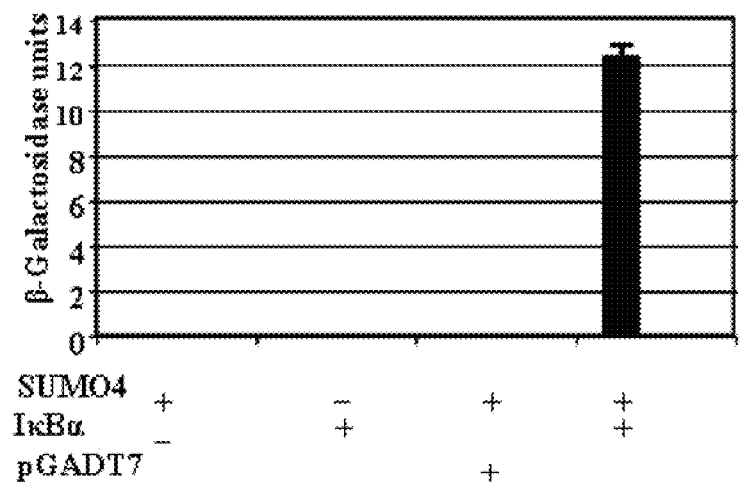
FIGS. 4A, 4B, and 4C show data suggesting that IκBα is a substrate for SUMO4 interaction and/or modification.

One clone was identified to strongly interact with SUMO4, and it was determined that it originated from the IκBα gene (FIG. 4A). To confirm this observation, a His-tagged SUMO4 expression plasmid (pcDNA3.1/SUMO4) or empty vector was transfected into HEK293 cells. After 36 hours transfection, the cells were harvested for immunoprecipitation using agarose beads conjugated with a rabbit His polyclonal antibody (Santa Cruz). Cells were lysed in SDS and diluted 1:4 in PBS/0.5% NP40 plus complete protease inhibitors before incubation for 14 hours at 4° C. with the antibody coated beads. The beads were collected and washed five times with ice-cold PBS/0.5% NP40 plus complete protease inhibitor cocktail. The antigen-antibody complexes were recovered by boiling in SDS sample buffer. The immunoprecipitates were fractionated by electrophoresis in 13% polyacrylamide gel and transferred to a PVDF membrane as reported (Wang et al. 2003).

Figure 4B:
Figure 4C:
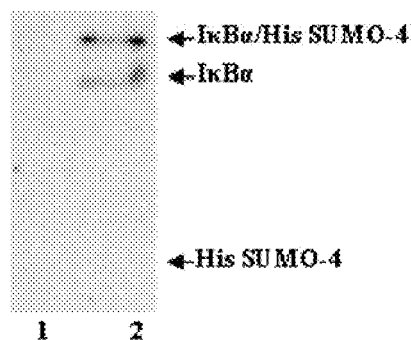

Western blots were carried out as described previously. The membranes were probed with mouse monoclonal H is (Clontech) and IκBα (Santa Cruz) antibodies, respectively, and developed using an ECL kit (Amersham). The Western analyses clearly showed that SUMO4 conjugates with IκBα in vivo (FIG. 4B and FIG. 4C). These results suggest that IκBα is a substrate for SUMO4 modification.

Since IκBα is a negative feedback regulator in the NFκB signaling pathway (Desterro et al., 1998; Karin, 1999), we explored the role of SUMO4 in the regulation of NFκB transcriptional activity. HEK293 and HeLa cells were maintained in exponential growth in Dulbecco's modified Eagle's medium, containing 10% fetal calf serum. U937 cells were grown in RPMI1640 medium supplemented with 10% fetal calf serum. An NFκB-dependent luciferase reporter (3enh conA luc) was cotransfected into HEK293 cells along with a SUMO4 expression construct (pcDNA3.1), and the reporter activity was measured after treatment of the cells with an NFκB3 activator, TNFα, or IL-1β. The plasmid DNAs (1-2 µg) were transfected for 14 hours in subconfluent cells in six-well plates using Lipofectamine (Invitrogen) and cultured for additional 36 hours. For stimulation, the transfected cells were incubated for 8 hours with medium containing TNFα or IL-1β (10 ng/ml, Sigma), or control medium. Subsequently, the cells were collected and the luciferase activity measured using the Dual-Luciferase Reporter Assay System (Promega).

Figure 5A:
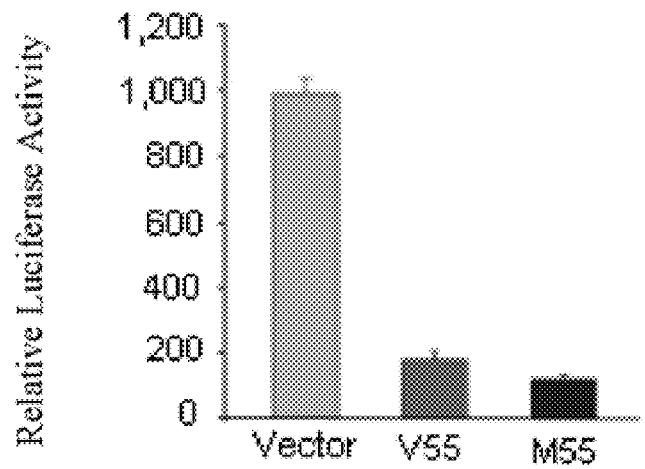
FIGS. 5A and 5B are graphs showing relative activity of a luciferase reporter. HEK293 cells were co-transfected with dual luciferase reporters (an NFκB-dependent reporter and a reference reporter) and either a control plasmid (empty pcDNA3.1 vector) or the indicated SUMO4 expression plasmids. Transfected cells were stimulated with TNFα or cultured in control medium and dual luciferase activities were measured in cell lysates.
Figure 5B:
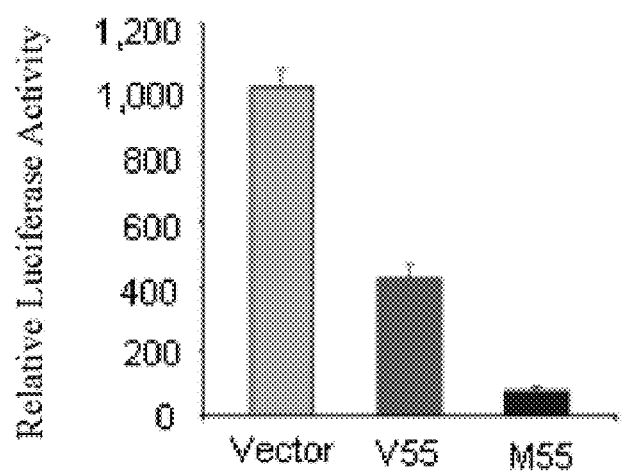

We found that the relative luciferase activity for the cells co-transfected with an empty vector (2098±204) was 11.5-fold higher than the cells co-transfected with SUMO4 (214±29) (P 0.00009) (FIG. 5A), indicating that SUMO4 plays a negative regulatory role in the NFκB signaling pathway. The next important question was whether the M55V substitution has an impact on the regulation of NFκB transcriptional activity. We tested this possibility by similar transfection assays in HEK293 cells. It was found that M55V SUMO4 showed 5,6-fold higher reporter activity than M55 SUMO4 (P=0.02, FIG. 5B). Similar results were also obtained in transfection assays with HeLa and U937 cells (data not shown).

The effect of the M55V substitution on NFκB transcriptional activity was further studied by measuring mRNA levels of an NFκB-dependent gene, IL-12p40. Our results predict that individuals with the A/A genotype (Met) should have lower IL-12p40 expression than that with the A/G and G/C genotypes. We used quantitative RT-PCR to measure the relative level of the IL-12p40 mRNA transcribed upon IL-1'-induced NFκB activation in peripheral blood mononuclear cells (PBMC). PBMC from four individuals with A/A, five individuals with A/G and four individuals with C/G genotypes were examined. PBMC from each individual were isolated by IsoPrep (Robins Scientific) and seeded in duplicate in a six-well plate (5×10⁶ cells per well) and cultured in RPMI1640 with 10% fetal calf serum for 12 hours. After treatment of the cells from one well of each individual with IL-1β (10 ng/ml) for 8 hours, all of the cells were collected for RNA extraction using the Qiagen protocol including DNase treatment. RNA concentration was measured on the Bioanalyzer (Agilent Technologies). Reverse transcription was carried out according to the Superscript protocol (Invitrogen). Primers for β-actin and IL-12p40 were used to amplify target sequences with 22 (β-actin) or 25 (IL-12p40) cycles at 30 seconds at 95° C., 30 seconds at 62° C., and 30 seconds at 72° C. each. The relative intensity for each corresponding band was characterized by the ChemiImager System (Alpha Innotech Corp.) and normalized by background intensity. The relative IL-12p40 expression levels were defined by a ratio with β-actin.

Figure 6A:
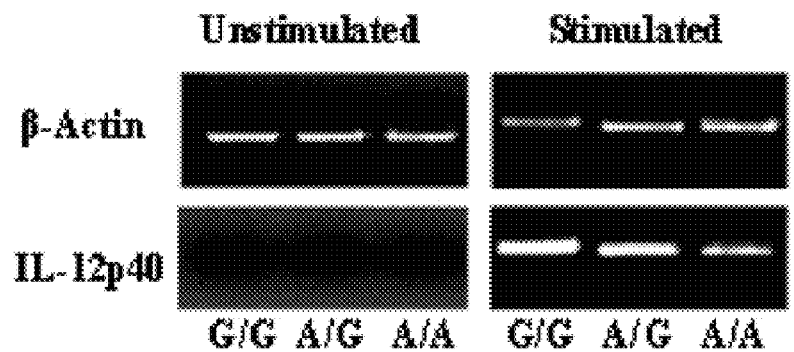
FIGS. 6A and 6B show results of quantitative RT-PCR assays of IL-12p40 expression Peripheral blood mononuclear cells (PBMC) from four individuals with the homozygous 6 (Val) allele, four individuals with the homozygous A (Met) allele, and five individuals with the heterozygous (A/G) genotype were included for the study. The PBMC were stimulated with IL-1β for 8 hours and then harvested for IL-12p40 expression analysis by quantitative RT-PCR. The relative mRNA levels for each individual were defined by the ratio of net intensity between IL-12p40 and β-actin.
Figure 6B:
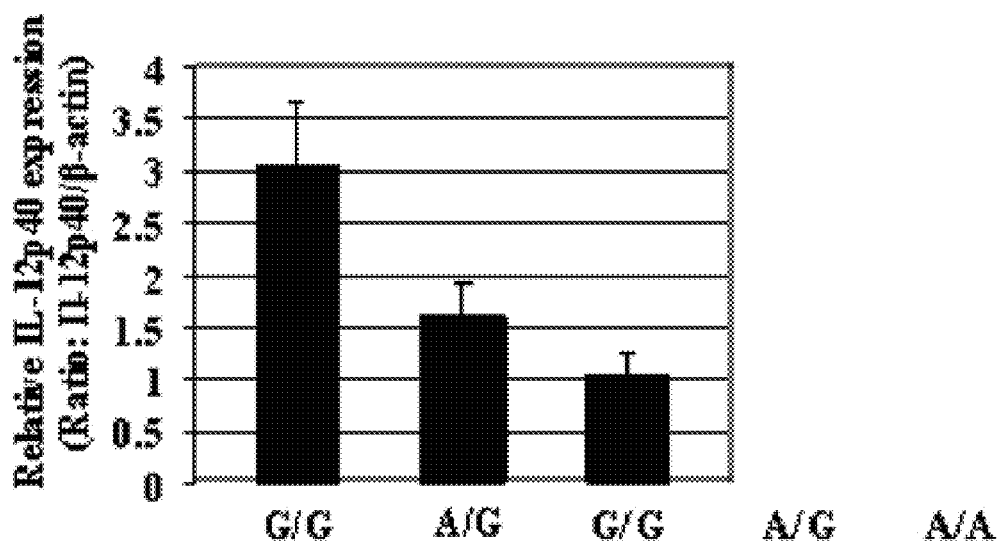

IL-12p40 was undetectable in unstimulated PBMC, but high levels of expression were observed after treatment with IL-1β (FIG. 6A). As expected, individuals with the G/G genotype, which is associated with increased T1D susceptibility, have 3-fold higher expression (3.06±0.6) than individuals with the A/A genotype (1.05±0.2, P=0.01). Individuals with the A/G genotype (1.61±0.3) also showed 53% higher IL-12p40 expression than individuals with the A/A genotype (FIG. 6B). Thus, the M55V substitution of SUMO4 appears to have functional consequences on NFκB transcription activity.

Upon signal-induced activation, NFκB activates transcription for three groups of genes, 1) auto-regulatory genes (p50 & p65), 2) immune response genes (e.g. IL-1, -2, -6, -12, TNFα and IL-2Rα), and 3) negative feedback regulators (e.g. IκBα) that tightly control immune response (May & Ghosh, 1998; Matsuda et al., 2003; Baldwin, 1996). Our results suggest a novel pathway for T1D pathogenesis. In this model, SUMO4 stabilizes IκBα from signal-induced degradation by its modification. The M55V substitution of SUMO4 may affect its modification capacity for IκBα and lead to elevated levels of activated NFκB, which activates transcription for genes implicated in the development of T1D.

Example 6

SUMO4 Inhibits NFκB Transcriptional Activity

SUMO4 is the fourth member for the SUMO family with specific expression in kidney and immune tissues. Previously, we have found that SUMO4 conjugates with IκBα and negatively regulates NFκB transcriptional activity. We performed luciferase assays in HEK293 cells cotransfected with an NFκB-dependent luciferase reporter (3enh conA luc) along with the SUMO4 expression construct (pcDNA3.1). We observed that cells cotransfected with an empty vector have 8.4-fold higher reporter activity than cells cotransfected with SUMO4 under unstimulated conditions, while the reporter activity was almost 13-fold higher after IL-1β stimulation. We also found that ectopic SUMO4 expression significantly inhibits the expression of IL-12p40, an NFκB-dependent gene, upon IL-1β stimulation. These results suggest that SUMO4 could be an endogenous negative regulator for NFκB.

Figure 8:
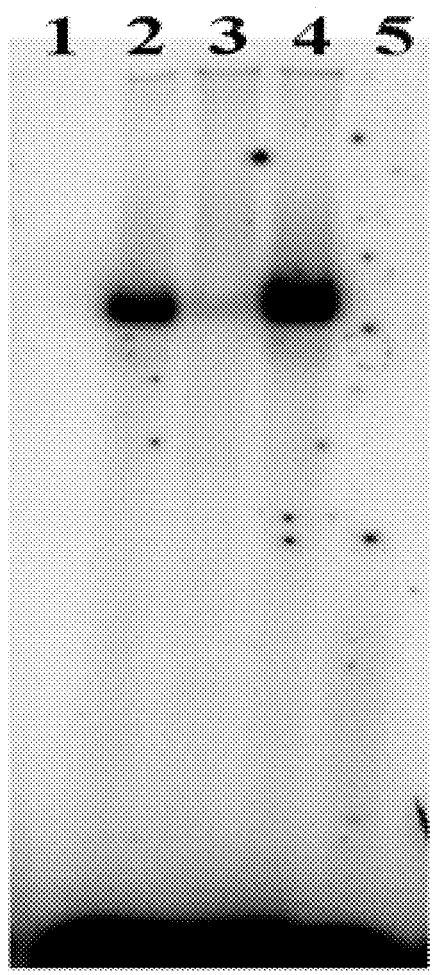
FIG. 8 shows that SUMO4 inhibits NFκB binding activity. The same amount of nuclear proteins were loaded for each lane. Lane 1: proteins from untransfected cells only; lane 2: cells transfected with SUMO4+hot probe; lane 3: cells transfected with vector+hot probe+cold probe; Lane 4: the same proteins as lane 3+hot probe; lane 5: hot probe only.

To further demonstrate the effect of SUMO4 on NFκB, we investigated NFκB binding activity using HEK293 cell lysates with and without ectopic SUMO4 by electrophoretic mobility shift assay (EMSA). HEK293 cells were transfected with SUMO4 and empty vector (pcDNA3.1), respectively, and nuclear extracts from these cells were prepared after TNFα stimulation. EMSA was performed with a kit (Roche) using a $\alpha$-$^{32}$P labeled NFκB probe as reported. As shown in FIG. 8, SUMO4 expression significantly inhibited NFκB DNA bind activity. Cells transfected with an empty vector (lane 4) had about 3-fold higher DNA binding activity than that of cells transfected with SUMO4 (lane 2)

Example 7

SUMO4 Modifies IκBα

Figure 9A:
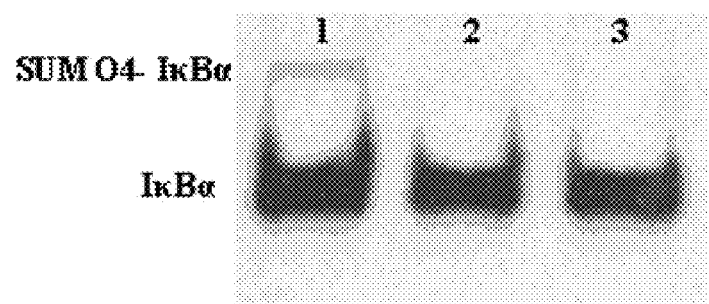
FIG. 9A: Conjugation assay using recombinant SAE1/SAE2 (E1) and Ubc9 (E2). The products were probed with an IκBα monoclonal antibody. Lane 1: the assay was performed with all components; Lane 2: the assay was performed without E1 and E; Lane 3: the assay was performed without SUMO4.
Figure 9B:
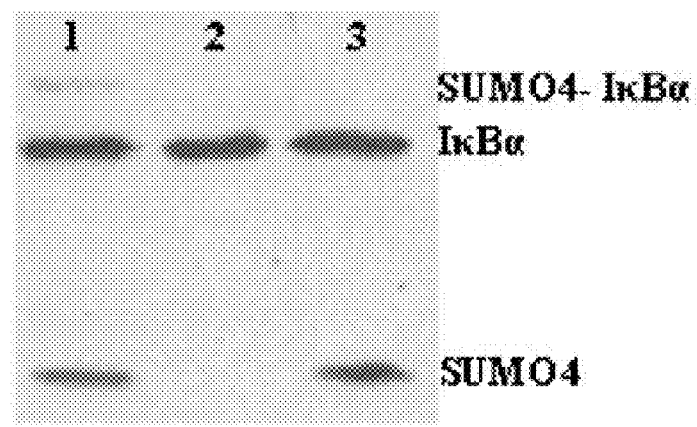
FIG. 9B: Conjugation assay using immunoprecipitated SAE1/SAE2 (E1) and Ubc9 (F2). The products were probed with a H is monoclonal antibody. H is antibody can recognize both SUMO4 and IκBα. Lane 1: the assay was performed with all components; Lane 2: the assay was performed without E1 and ES; Lane 3: the assay was performed without SUMO4. SUMO4 can only conjugate to IκBα in the presence of E1 and E2 (lane 1, the top band).

Next, we performed in vitro conjugation assays to determine that SUMO4 modifies IκBα. The assay was carried out with a kit (LAE Biotechnology Co. Ltd) in the presence of SUMO E1 (SAE1/SAE2) activating enzyme and E2 (Ubc9) conjugating enzyme with recombinant SUMO4-his and IκBα-his (purchased from ActiveMotif). Recombinant SUMO4 was expressed and purified using a pet32 vector (Novagen) according to the manufacturer's instruction. The assay was performed in 20-μl volumes containing SUMO4-His (1-μg), an ATP-regeneration system, buffer [50 mM Tris (pH7.5), 5 mM $MgCl_2$, 2 mM ATP, 10 mM creatine phosphate, 3.5 units/ml creatine kinase], and 0.6 units/ml inorganic pyrophophotase using 2-μg IκBα-his as substrate. The assays also contained 100-ng SAE1/SAE2 (E1) and 200-ng of Ubc9 (E2). The reactions were incubated at 37° C. for 2 hrs. After the reaction, the products were analyzed by Western blotting probed with IκBα or H is antibodies. As indicated in FIG. 9, SUMO4 conjugates to IκBα in the presence of either recombinant E1 and E2 enzymes (FIG. 9A, lane 1, the top band) or the immunoprecipitated E1 and E2 enzymes (FIG. 9B, lane 1, top band).

Example 8

An NFκB Binding Site is Found in the SUMO4Promoter Region

Figure 10A:
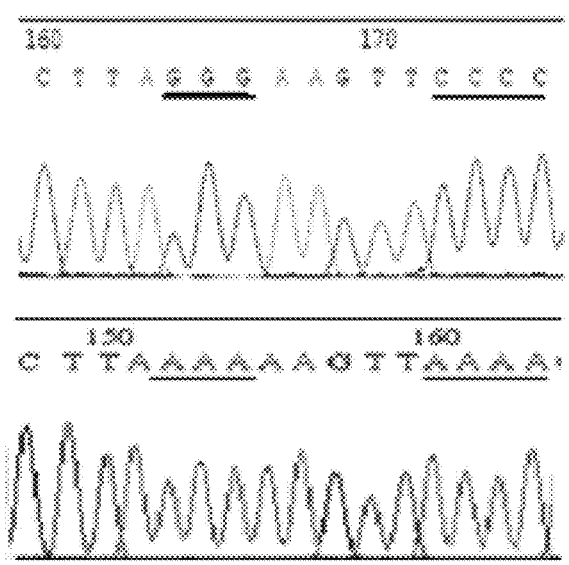
FIG. 10A: Site-directed mutagenesis results (SEQ ID NOS:25 and 26).
Figure 10B:
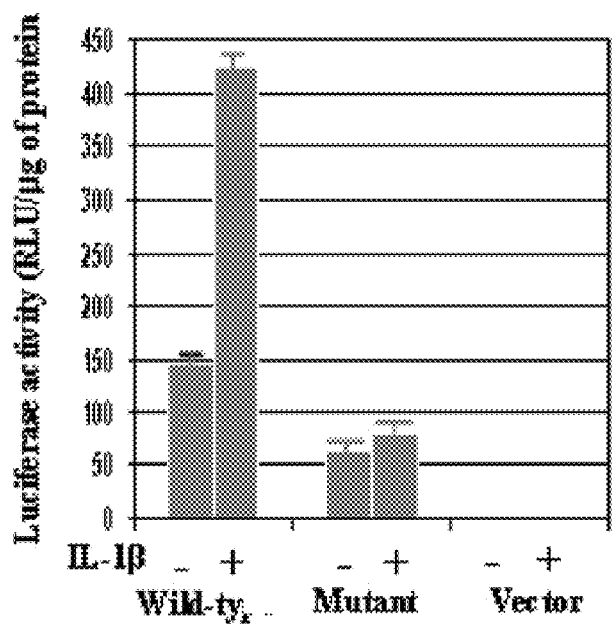
FIG. 10B: Relative reporter activity before/after IL-1β, stimulation. Vector: promoterless plasmid.

Interestingly, an NFκB binding site was found in the SUMO4 promoter region, suggesting that NFκB could regulate SUMO4 expression. To test this hypothesis, we have cloned the SUMO4 promoter into a PGL2-Basic promoter reporter vector (Promega), which lacks a eukaryotic promoter and enhancer sequences but carries the luciferase gene (luc). The promoter sequence consists of 900 bp of DNA containing the NFκB binding motif TTAGGGAAGTTCCCC (SEQ ID NO:12), core promoter sequence TGAATGATTTTAAAAA-CAGATCTGGCAGCAGCCAATGGCAGGCCCCAA (SEQ ID NO:13) and several putative regulatory elements. Site-directed mutagenesis was employed to mutate the NFκB binding site (SEQ ID NO:12) from GGGAAGTTCC (residues 5-14 of SEQ ID NO:25, FIG. 10A, upper panel) to AAAAAGTTAA (residues 5-14 of SEQ ID NO:26, FIG. 10A, lower panel). The wild-type and mutant promoter plasmids were transfected into HEK293 cells, respectively, and the relative reporter activities (normalized by TK reporter) were assayed before and after IL-1β stimulation. Transfection of an empty vector (promoterless) was used as a control. As we expected, the luciferase reporter activity significantly increased upon IL-1β stimulation in the cells transfected with the wild-type SUMO4 promoter (by 2.8 fold, P=0.03), while there was no significant change for the reporter activity in the cells transfected with the mutant SUMO4 promoter. Furthermore, even in unstimulated cells, the wild-type reporter activity was much higher (2.4 fold) than that of the mutant promoter (FIG. 10B), suggesting that even in the normal conditions, NFκB-dependent SUMO4 expression is probably required to tightly control NFκB activity.

Example 9

NFκB Binds to SUMO4 Promoter In Vivo

Figure 11A:
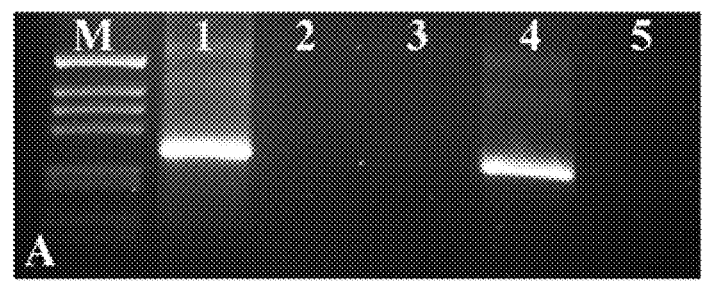
FIG. 11A: PCR amplification of ChIP products using SUMO4 promoter primers covering the NFκB binding site. Lane 1: products from ChiP assay carried out with NFκB P65 monoclonal antibody; lane 2: products from ChIP assay without addition of antibody; lane 3: products from ChIP assay performed with β-actin antibody; lane 4: genomic DNA; lane 5: negative control (without DNA).
Figure 11B:
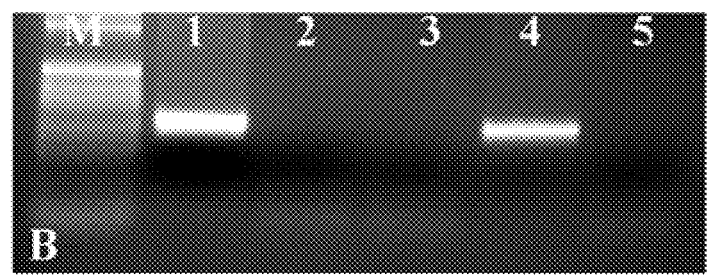
FIG. 11B PCR amplification of ChIP products with TNFα promoter primers covering the NFκB binding site.
Figure 11C:
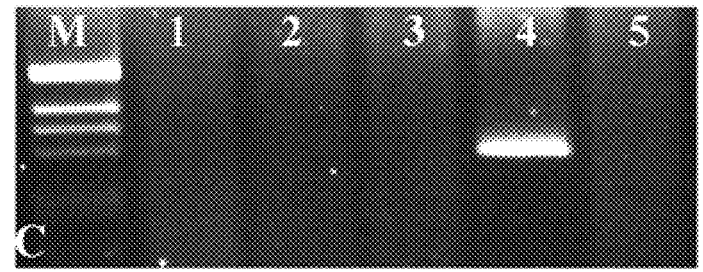
FIG. 11C: PCR amplification of ChIP products using ACDP1 promoter primers which does not contain NFκB binding site. PCR templates used for each lane of B and C are corresponding to each lane of A.

To further demonstrate that NFκB binds to SUMO4 promoter in vivo, we did chromatin immunoprecipitation (ChIP) assay using a kit from Upstate. Monoclonal NFκB P65 antibody was purchased from Santa Cruz. $2 \times 10^6$ HEK 293 cells were first stimulated with IL-1β for 8 hrs and then fixed with formaldehyde. After washing the cells with ice cold PBS containing protease inhibitors several times, the cells were collected and resuspended in 200 μl of SDS lysis buffer and incubated on ice for 10 min. The cell lysates were then subjected to sonication to shear DNA to lengths between 200 and 1000 bp on ice. Protein/DNA complexes were recovered by phenol/chloroformm extraction. NFrB/DNA complexes were then pulled down with the NFκB p65 antibody according to the manufacturer's instruction. To test the possibility of non-specific immunoprecipitation, we used a β-actin antibody as negative control. The immunoprecipitates were then used as templates for PCR amplification of SUMO4 promoter region containing the NFκB binding site. As shown in FIG. 11A lane 1, immunoprecipitates obtained from NFκB p65 antibody yielded a corresponding positive band (as compared to genomic DNA, lane 4), while the products obtained from β-actin antibody yielded negative results (lane 3), suggesting that NFκB binds to SUMO4 promoter in vivo. To further demonstrate the specificity of this ChIP assay, we tested a known NFκB regulated gene, TNFα. The TNFα promoter has been previously characterized containing the NFK3 binding site. The primers for TNFα promoter covering the known NFκB binding site were used to amplify the same templates used in FIG. 11A. As expected, we obtained consistent results as SUMO4, only NFκB p65 antibody can pull down TNFα promoter (FIG. 11B, lane 1). We also tested ACDP1 promoter which does not contain NFκB binding site, as can be seen from FIG. 11C, none of the immunoprecipitates yielded positive results. These observations suggest that upon activation, NFκB not only activates transcription for immune responsive genes, but also activates SUMO4 expression to tightly control the immune response. Therefore, SUMO4 could be a negative feedback regulator for NFκB transcriptional activity.

Example 10

Evidence for a Role of SUMO4 in the Regulation of Oxidative Stress in Diabetes

Figure 12A:
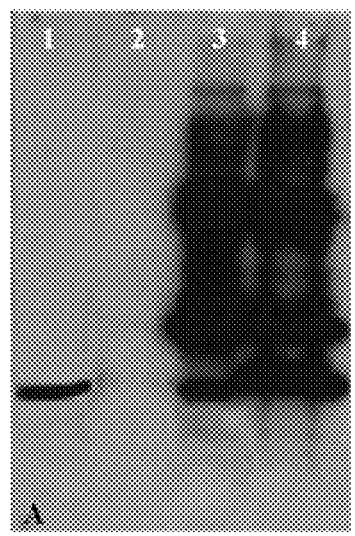
FIG. 12A: SUMO4 immunoprecipitates probed with H is monoclonal antibody. Lane 1: His tagged recombinant SUMO4; lane 2: cell lysates from untransfected cells; lane 3 and 4: SUMO4 immunoprecipitates.
Figure 12B:
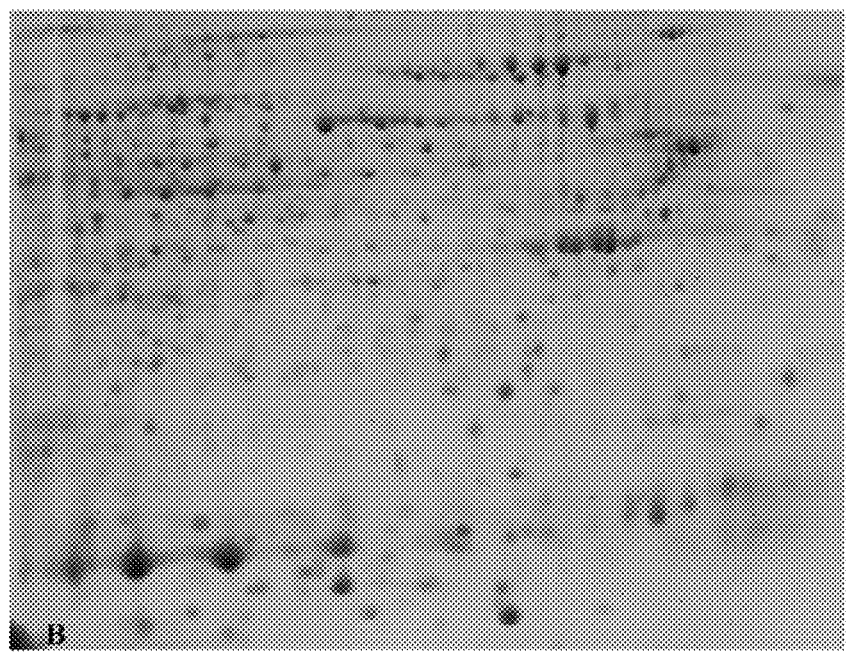
FIG. 12B: 2D PAGE results for the SUMO4 immunoprecipitates.

In order to fully understand the role of SUMO4 in diabetes and its complications, we investigated its target proteins in HEK293 cells under oxidative stress. We first established cell lines stably transfected with SUMO4. For this purpose, HEK293 cells were transfected with His-SUMO4-pcDNA3.1 plasmid and then selected with G418 for four weeks. Selected cell clones were then tested by Western blots for ectopic SUMO4 expression. Two clones were identified with high levels of ectopic SUMO4 expression. These two clones were cultured in large scale (five 75 $mm^2$ flasks for each) to obtain enough cells for experiments. The cells were treated with $H_2O_2$ (100 μM) for 4 hrs to induce oxidative stress. Cell lysates were collected, and His-tagged SUMO4 protein complexes were isolated using the His Tagged Protein Isolation Kit (MACS), according to manufacture's instruction. Briefly, cell lysates were loaded into separate μ Columns containing the anti-His MicroBeads. The MicroBeads bind specifically to H is epitope. The magnetically labeled proteins were then retained on the μ Column placed in the magnetic field of a μMACS Separator. After five high stringent washes, the SUMO4 protein complexes were eluted out as instructed. The resultant proteins were then subjected to Western blot analysis with the His antibody provided within the kit. As shown in FIG. 12A, precipitates obtained from transfected clones showed His-tagged proteins (lane 3 & 4), while cell lysates from the untransfected HEK293 cells showed negative results (lane 2). Lane 1 was a positive control with recombinant His-tagged SUMO4. We then combined the precipitates from the transfected clones and used 150 µg for 2D PAGE analysis. As shown in FIG. 12B, Sybro Rubby staining revealed a total of 364 protein spots on the 2D gel. These spots were then analyzed for their identity (protein ID) by MALDI-TOF/TOF analysis. We have identified a total of 90 proteins (Table 8). Since sumoylation either changes the mobility or electric charge of the substrate, therefore, an identical protein after sumoylation will have multiple spots on the 2-D gel. The proteins listed in Table 8 have at least two different spots on the 2D gel. For example, four adjacent spots showed same ID corresponding to peroxiredoxin 3. 56 spots failed to obtain protein ID due to the limitation of protein amount present in each spot.

An interesting group of proteins that were SUMO4-conjugated is the antioxidant enzymes including Cu/ZnSOD and catalase. Some molecular chaperones (e.g., HSP9B and Grp58) were also sumoylated in response to oxidative stress. Another group of SUMO4 substrates was the proteins involved in DNA repair and synthesis and protein degradation. Our study also identified SUMO4 sumoylation of proteins involved in glucose metabolism. These results suggest that SUMO4 could be involved in the regulation of intracellular ROS degradation and glucose metabolism during diabetic hyperglycemia. Of note, many of the target proteins identified for SUMO4 are also substrates for other SUMO members identified from previous studies.

TABLE 8

SUMO4 substrates identified in HEK293 cells under oxidative stress

| Protein classification | Accession NO | No. of peptide hits | Function |
| --- | --- | --- | --- |
| Anti-stress proteins | | | |
| Cu/Zn superoxide dismutase | 134611 | 4 | antioxidant enzyme |
| catlase | 4557014 | 11 | antioxidant enzyme |
| chain A erythrocyte catalase | 7245756 | 9 | antioxidant enzyme |
| thioredoxin-like protein | 5730104 | 7 | antioxidant enzyme |
| thioredoxin-like 1 | 4759274 | 8 | antioxidant enzyme |
| thioredoxin peroxidase | 5453549 | 11 | antioxidant enzyme |
| Trp26 | 21361837 | 11 | antioxidant defense |
| peroxiredoxin 6 | 4758638 | 12 | antioxidant enzyme |
| peroxiredoxin 3 | 5802974 | 9 | antioxidant enzyme |
| Glutathione S-transferase | 2204207 | 10 | antioxidant enzyme |
| Peroxiredoxin 2 | 2507169 | 11 | antioxidant enzyme |
| Valson-containing protein | 6005942 | 13 | export of ER proteins into the cytosol |
| Aconitase 2, mitochondrial | 20072188 | 15 | oxidation |
| HSP 70 kDa protein 5 (Grp) | 16507237 | 28 | chaperone |
| HSP 70 kDa protein isoform 1 | 5729877 | 26 | chaperone |
| HSP 70 kDa protein 9B | 21040386 | 28 | chaperone |
| HSP 70 kDa protein 1B | 4885431 | 25 | chaperone |
| HSP70.1 | 462325 | 29 | chaperone |
| calreticulin precursor | 4757900 | 10 | chaperone |
| stress induced phosphoprotein 1 | 5803181 | 22 | Hsp70/Hsp90-organizing protein |
| 60 kDa HSP, mitochondrial | 129379 | 28 | chaperone |
| chaperone containing TCP1 zeta 1 | 4502643 | 13 | chaperone |
| Grp58 | 21361657 | 19 | chaperone |
| chaperone containing TCP1, eta | 5453607 | 16 | chaperone |
| chaperone containing TCP1, beta | 5453603 | 26 | chaperone |
| TXNDC4, ER | 18572267 | 14 | antioxidant defense |
| DnaJ protein homolog | 219588 | 8 | chaperone |
| ER-associated Hsp40 | 7706495 | 16 | co-chaperone |
| DNA repair and synthesis | | | |
| Lamin B1 | 15126742 | 18 | DNA replication |
| Lamin A/C | 5031875 | 33 | DNA replication |
| DNA topoisomerase II, alpha | 19913406 | 11 | DNA repair and maintenance |
| 67 kDa lamin receptor | 250127 | 9 | DNA replication |
| phosphoribosyl pyrophosphate synthetase | 14506127 | 8 | DNA synthesis |
| inorganic pyrophosphatase | 11056044 | 17 | chromatin structure |
| Protein degradation | | | |
| ubiquitin-conjugating enzyme E2 variant 1 isoform a | 40806164 | 7 | ubiquitylation |
| proteasome 26S ATPase subunit 2 | 4506209 | 11 | protein degradation |
| Kunitz-type protease inhibitor | 2598968 | 8 | protein degradation |
| protease (prosome, macropain) 26S subunit, ATPase 5 | 7110703 | 16 | protein degradation |

TABLE 8-continued

SUMO4 substrates identified in HEK293 cells under oxidative stress

| Protein classification | Accession NO | No. of peptide hits | Function |
|---|---|---|---|
| Metabolism | | | |
| Pyruvate kinase | 478822 | 20 | glucose use |
| glucose-6-phosphate dehydrogenase | 21614520 | 18 | glucose use |
| IMP dehydrogenase 2 | 124419 | 12 | glucose metabolism |
| phosphoglycerate dehydrogenase | 23308577 | 20 | glucose metabolism |
| 3-phosphoglycerate dehydrogenase | 2674062 | 10 | glucose metabolism |
| ATP synthase beta chain, mitochondria | 114549 | 16 | glucose metabolism |
| glutathione reductase | 10835189 | 11 | glucose metabolism |
| protein disulfide isomerase-related protein 5 | 1710248 | 9 | glucose metabolism |
| gamma enolase | 182118 | 7 | glucose metabolism |
| enolase 1 | 4503571 | 14 | glucose metabolism |
| Mitochondrial Creatine Kinase | 7767133 | 12 | glucose metabolism |
| NADP-dependent isocitrate dehydrogenase | 3641398 | 13 | glucose metabolism |
| phosphoglycerate kinase 1 | 4505763 | 18 | glucose metabolism |
| acyl-Coenzyme A dehydrogenase | 4557231 | 14 | glucose metabolism |
| aldolase A | 28614 | 16 | glucose metabolism |
| isocitrate dehydrogenase 3 (NAD+) α precursor | 5031777 | 10 | glucose metabolism |
| lactate dehydrogenase B | 4557032 | 5 | glucose metabolism |
| glyceraldehyde-3-phosphate dehydrogenase | 7669492 | 10 | glucose metabolism |
| similar to Esterase D | 20547663 | 7 | glucose metabolism |
| carbonate hydrolyase | 13096560 | 9 | cell respiration |
| platelet-activating factor acetylhydrolase, isoform Ib | 4505587 | 11 | acetyl metabolism |
| Others | | | |
| voltage-dependent anion channel 1 | 4507879 | 11 | mitochondrial ion channel |
| stomatin (EPB72)-like 2 | 7305503 | 14 | ion channel regulation |
| nuclear chloride ion channel protein | 2073569 | 7 | ion channel |
| moesin/anaplastic lymphoma kinase fusion protein | 14625824 | 22 | cell signaling |
| GMP synthetase | 4504035 | | cell signaling |
| guanine nucleotide binding protein | 5174447 | 14 | transcriptional regulation |
| prohibition | 4505773 | 13 | transcriptional regulation |
| WD-repeat protein | 5031729 | 9 | transcriptional regulation |
| zinc finger protein 259 | 4508021 | 10 | transcriptional regulation |
| hnRNP-L | 52632383 | 15 | RNA binding, processing |
| hnRNP K | 13384620 | 15 | RNA binding, processing |
| hnRNP H1 | 5031753 | 12 | RNA binding, processing |
| hnRNP F | 4826760 | 6 | RNA binding, processing |
| hnRNP D | 870747 | 10 | RNA binding, processing |
| non-POU domain containing, octamer-binding | 7657383 | 14 | RNA binding |
| unr-interacting protein | 20149592 | 9 | RNA binding |
| splicing factor 3b, subunit 4 | 5032069 | 5 | RNA splicing |
| TUFM | 21359837 | 17 | mitochondrial regulation |
| mitochondrial ribosomal protein S22 | 9910244 | 14 | ribosomal protein |
| Vimentin | 4507895 | 25 | cytoskeletal regulation |
| tubulin alpha 6 | 14389309 | 11 | cytoskeletal regulation |
| actin gamma 1 | 4501887 | 14 | cytoskeletal regulation |
| anti-colorectal carcinoma heavy chain | 425518 | 11 | cell growth related protein |
| proliferation-associated 2G4 | 5453842 | 14 | cell growth |
| eukaryotic translation initiation factor 3 | 4503513 | 11 | protein synthesis |
| TPMsk3 | 19072649 | 12 | signal transduction |
| IκBα | 10092619 | 12 | signal transduction |
| Rho GDP dissociation inhibitor | 4757768 | 9 | GDP-GTP exchange |

TABLE 8-continued

SUMO4 substrates identified in HEK293 cells under oxidative stress

| Protein classification | Accession NO | No. of peptide hits | Function |
|---|---|---|---|
| SUMO4 | 50400081 | 4 | sumoylation |
| Pro2675 | 7770217 | 12 | unknown |
| hypothetical protein | 12652799 | 16 | unknown |
| Unknown protein | 12804225 | 18 | unknown |

REFERENCES

1. Onengut-Gumuscu, S. & Concannon, P. Mapping genes for autoimmunity in humans: Type 1 diabetes as a model. Immunol. Rev. 190, 182-194 (2002).
2. Pociot, F. & McDermott, M. F. Genetics of Type 1 diabetes mellitus. Genes Immun. 3, 235-249 (2002).
3. Twells, R. C. et al. Linkage and association mapping of the LRP5 locus on chromosome 11q13 in Type 1 diabetes. Hum. Genet. 113, 99-105 (2003).
4. Twells, R. C. et al. The sequence and gene characterization of a 400-kb candidate region for IDDM4 on chromosome 11q3. Genomics 72, 231-242 (2001).
5. Nakagawa, Y. et al. Fine mapping of the diabetes-susceptibility locus, IDDM4, on chromosome 11q13. Am. J. Hum. Genet. 63, 547-556 (1998).
6. Eckenrode, S. et al. Fine-mapping of the Type 1 diabetes locus (IDDM4) on chromosome 11q and evaluation of two candidate genes (FADD and GALN) by affected sibpair and linkage-disequilibrium analyses. Hum. Genet. 106, 14-18 (2000).
7. Luo, D. F. et al. Affected-sib-pair mapping of a novel susceptibility gene to insulin-dependent diabetes mellitus (IDDM8) on chromosome 6q25-q27. Am. J. Hum. Genet. 57, 911-919 (1995).
8. Luo, D. F. et al. Confirmation of three susceptibility genes to insulin-dependent diabetes mellitus: IDDM4, IDDM5 and IDDM8. Hum. Mol. Genet. 5, 693-698 (1996).
9. Owerbach, D. Physical and genetic mapping of IDDM8 on chromosome 6q27. Diabetes 49, 508-512 (2000).
10. Davies, J. L. et al. A genome-wide search for human Type 1 diabetes susceptibility genes. Nature 371, 130-136 (1994).
11. Delepine, M. et al. Evidence of a non-MHC susceptibility locus in type I diabetes linked to HLA on chromosome 6. Am. J. Hum. Genet. 60, 174-187 (1997).
12. Jiang, Z., Ninomiya-Tsuji, J., Qian, Y., Matsumoto, K., & Li, X. Interleukin-1 (IL-1) receptor-associated kinase-dependent IL-1-induced signaling complexes phosphorylate TAK1 and TAB2 at the plasma membrane and activate TAK1 in the cytosol. Mol. Cell Biol. 22, 7158-7167 (2002).
13. Qian, Y., Commane, M., Ninomiya-Tsuji, J., Matsumoto, K., & Li, X. IRAK-mediated translocation of TRAF6 and TAB2 in the interleukin-1-induced activation of NFkappa B. J. Biol. Chem., 276, 41661-41667 (2001).
14. Takaesu, G. et al. TAB2, a novel adaptor protein, mediates activation of TAK1 MAPKKK by linking TAK1 to TRAF6 in the IL-1 signal transduction pathway. Mol. Cell. 5, 649-658 (2000).
15. Takaesu, G. et al. Interleukin-1 (IL-1) receptor-associated kinase leads to activation of TAK1 by inducing TAB2 translocation in the IL-1 signaling pathway. Mol. Cell Biol. 21, 2475-2484 (2001).
16. Best, J. L. et al. SUMO-1 protease-1 regulates gene transcription through PML. Mol. Cell 10, 843-855 (2002).
17. Joseph, J., Tan, S. H., Karpova, T. S., McNally, J. G., & Dasso, M. SUMO-1 targets RanGAPI to kinetochores and mitotic spindles. J. Cell Biol. 156, 595-602 (2002).
18. Melchior, F. & Hengst, L. SUMO-1 and p53. Cell Cycle 1, 245-249 (2002).
19. Rogers, R. S., Horvath, C. M., & Matunis, M. J. SUMO modification of STATI and its role in PIAS-mediated inhibition of gene activation. J. Biol. Chem. (2003).
20. Ross, S., Best, J. L., Zon, L. I., & Gill, G. SUMO-1 modification represses Sp3 transcriptional activation and modulates its subnuclear localization. Mol. Cell 10, 831-842 (2002).
21. Tian, S., Poukka, H., Palvimo, J. J., & Janne, O. A. Small ubiquitin-related modifier-1 (SUMO-1) modification of the glucocorticoid receptor. Biochem. J. 367, 907-911 (2002).
22. Desterro, J. M., Rodriguez, M. S., & Hay, R. T. SUMO-1 modification of IkappaBalpha inhibits NF-kappaB activation. Mol. Cell 2, 233-239 (1998).
23. Matunis, M. J. On the road to repair: PCNA encounters SUMO and ubiquitin modifications. Mol. Cell 10, 441-442 (2002).
24. Karin, M. How NF-kappaB is activated: the role of the IkappaB kinase (IKK) complex. Oncogene 18, 6867-6874 (1999).
25. May, M. J. & Ghosh, S. Signal transduction through NF-kappa B. Immunol. Today 19, 80-88 (1998).
26. Matsuda, A. et al. Large-scale identification and characterization of human genes that activate NF-kappaB and MAPK signaling pathways. Oncogene 22, 3307-3318 (2003).
27. Baldwin, A. S., Jr. The NF-kappa B and I kappa B proteins: new discoveries and insights. Annu. Rev. Immunol. 14, 649-683 (1996).
28. Deng, G. Y., Muir, A., Maclaren, N. K., & She, J. X. Association of LMP2 and LMP7 genes within the major histocompatibility complex with insulin-dependent diabetes mellitus: population and family studies. Am. J. Hum. Genet. 56, 528-534 (1995).
29. Spielman, R. S., McGinnis, R. E., & Ewens, W. J. Transmission test for linkage disequilibrium: the insulin gene region and insulin-dependent diabetes mellitus (IDDM). Am. J. Hum. Genet. 52, 506-516 (1993).
30. Wang, C. Y. et al. Molecular cloning and characterization of a novel gene family of four ancient conserved domain proteins (ACDP). Gene 306, 37-44 (2003).
31. Guo, D. et al. A functional variant of SUMO4, a new I kappa B alpha modifier, is associated with type 1 diabetes. Nat. Genet. 36, 837-841 (2004).
32. Rowland, T. L. et al. Differential effect of thalidomide and dexamethasone on the transcription factor NF-kappa B. Int. Immunopharmacol. 1, 49-61 (2001).

33. Manza, L. L. et al. Global Shifts in Protein Sumoylation in Response to Electrophile and Oxidative Stress. *Chem. Res. Toxicol.* 17, 1706-1715 (2004).
34. Vertegaal, A. C. et al. A proteomic study of SUMO-2 target proteins. *J. Biol. Chem.* 279, 33791-33798 (2004).

APPENDIX

Nucleic Acid Sequence of SUMO4 M55V from *Homo sapiens*

(SEQ ID NO: 1)
ATGGCCAACGAAAAGCCCACAGAAGAAGTCAAGACTGAGAACAACAATCA
TATTATTTGAAGGTGGCGGGACAGGATGGTTCTGTGGTGCAGTTTAAGAT
TAAGAGGCAGACACCACTTAGTAAACTAATGAAAGCCTATTGTGAACCAC
GGGGATTGTCAGTGAAGCAGATCAGATTCCGATTTGGTGGGCAACCAATC
AGTGGAACAGACAAACCTGCACAGTTGGAAATGGAAGATGAAGATACAAT
TGATGTGTTTCAACAGCCTACGGGAGGTGTCTACTGA

Deduced Amino Acid Sequence of SUMO4 M55V from *Homo sapiens*

(SEQ ID NO: 2)
MANEKPTEEVKTENNNHINLKVAGQDGSVVQFKIKRQTPLSKLMKAYCEP
RGLSVKQIRFRFGGQPISGTDKPAQLEMEDEDTIDVFQQPTGGVY

Nucleic Acid Sequence of SUMO4 from *Homo sapiens*

(SEQ ID NO: 3)
ATGGCCAACGAAAAGCCCACAGAAGAAGTCAAGACTGAGAACAACAATCA
TATTAATTTGAAGGTGGCGGGACAGGATGGTTCTGTGGTGCAGTTTAAGA
TTAAGAGGCAGACACCACTTAGTAAACTAATGAAAGCCTATTGTGAACCA
CGGGGATTGTCAATGAAGCAGATCAGATTCCGATTTGGTGGGCAACCAAT

CAGTGGAACAGACAAACCTGCACAGTTGGAAATGGAAGATGAAGATACAA
TTGATGTGTTTCAACAGCCTACGGGAGGTGTCTACTGA

Deduced Amino Acid Sequence of SUMO4 from *Homo sapiens*

(SEQ ID NO: 4)
MANEKPTEEVKTENNNHINLKVAGQDGSVVQFKIKRQTPLSKLMKAYCEP
RGLSMKQIRFRFGGQPISGTDKPAQLEMEDEDTIDVFQQPTGGVY

Nucleic Acid Sequence of SUMO4 M55V from *Homo sapiens* including 5' and 3' untranslated regions (SEQ ID NO: 11)
GAAGCAGCAGCTGAGGAGACTCCGGTGTTCACCATGGCCAACGAAAAGCC
CACAGAAGAAGTCAAGACTGAGAACAACAATCATATTAATTTGAAGGTGG
CGGGACAGGATGGTTCTGTGGTGCAGTTTAAGATTAAGAGGCAGACACCA
CTTAGTAAACTAATGAAAGCCTATTGTGAACCACGGGGATTGTCAATGAA
GCAGATCAGATTCCGATTTGGTGGGCAACCAATCAGTGGAACAGACAAAC
CTGCACAGTTGGAAATGGAAGATGAAGATACAATTGATGTGTTTCAACAG
CCTACGGGAGGTGTCTACTGAAAAAGGGAACCTGCTTCTTTACTCCAGAAC
GCTGTTCTTTAAAGACCAAGATTACTGCATTCTCAATTAGAAAACTGCAA
TTTGGTTCCACCACATTCTGACTACTACAGTATAGTTTTCTCTATTCTTT
TGTTTCCCCCTTCCACATTCTTTTATTATACATGAAGTAACTGGTATGTG
TACACAAGCATATTGCTTTTTTCTTCAAACCAAACAGCCAATGGTATGTT
TTGATTGACATCAAGTGGAGACAGGATGGGAAAAAATACTGATTCTGTGA
AAATACCCCCTTTATCCATTAGTGGCATGTTCATTCAGGTCTTATCTTTA
TATTCTAGTAAGTTATTTTGCTCTCACTGTTTTAACAAAAAAAAAAAAAA
AA

---

What is claimed is:

1. An isolated antibody that selectively binds to a polypeptide as defined in SEQ ID NO:2 over a polypeptide as defined in SEQ ID NO:4.

2. An isolated antibody that selectively binds to a SUMO4 polypeptide over other polypeptides, wherein the SUMO4 polypeptide is selected from the group consisting of:
   a) a polypeptide comprising an amino acid sequence as defined in SEQ ID NO:2 or SEQ ID NO:4; and
   b) a polypeptide comprising an amino acid sequence having at least 99% sequence identity with the SUMO4 polypeptide as defined in SEQ ID NO:2 or SEQ ID NO:4.

3. The antibody of claim 2, wherein the SUMO4 polypeptide comprises an amino acid sequence as defined in SEQ ID NO:2 or SEQ ID NO:4.

4. The antibody of claim 2, wherein the SUMO4 polypeptide comprises an amino acid sequence having at least 99% sequence identity with the polypeptide as defined in SEQ ID NO:2 or SEQ ID NO:4.

5. The antibody of claim 2, wherein the SUMO4 polypeptide comprises an amino acid sequence as defined in SEQ ID NO:2.

6. The antibody of claim 2, wherein the SUMO4 polypeptide comprises an amino acid sequence as defined in SEQ ID NO:4.

* * * * *